United States Patent
Benz et al.

(10) Patent No.: US 12,397,530 B2
(45) Date of Patent: Aug. 26, 2025

(54) PATTERNED, DENDRIMERIC SUBSTRATE SURFACES AND PRODUCTION AND USE THEREOF

(71) Applicant: KARLSRUHER INSTITUT FÜR TECHNOLOGIE, Karlsruhe (DE)

(72) Inventors: Maximilian Benz, Bruchsal (DE); Pavel A. Levkin, Eggenstein-Leopoldshafen (DE)

(73) Assignee: KARLSRUHER INSTITUT FÜR TECHNOLOGIE, Karlsruhe (DE)

( * ) Notice: Subject to any disclaimer, the term of this patent is extended or adjusted under 35 U.S.C. 154(b) by 1031 days.

(21) Appl. No.: 17/426,308

(22) PCT Filed: Jan. 30, 2020

(86) PCT No.: PCT/EP2020/052235
§ 371 (c)(1),
(2) Date: Jul. 28, 2021

(87) PCT Pub. No.: WO2020/164917
PCT Pub. Date: Aug. 20, 2020

(65) Prior Publication Data
US 2022/0119750 A1    Apr. 21, 2022

(30) Foreign Application Priority Data

Feb. 15, 2019 (DE) .......... 102019001137.6

(51) Int. Cl.
*B32B 15/00* (2006.01)
*B32B 3/14* (2006.01)

(52) U.S. Cl.
CPC ......... *B32B 15/00* (2013.01); *B32B 3/14* (2013.01)

(58) Field of Classification Search
CPC ...... C12M 25/06; C03C 17/002; C03C 17/30; B32B 3/14; B32B 15/00
USPC .................................................. 428/195.1
See application file for complete search history.

(56) References Cited

U.S. PATENT DOCUMENTS

| 6,077,500 A | 6/2000 | Dvornic et al. |
| 8,049,416 B2* | 11/2011 | Wolk .......... H10K 71/18 313/506 |
| 2003/0099930 A1* | 5/2003 | Graves ........... C12Q 1/6837 435/5 |
| 2008/0199960 A1* | 8/2008 | Juliano ............ C12N 15/111 435/325 |

(Continued)

OTHER PUBLICATIONS

International Search Report and Written Opining for PCT/EP2020/052235, 15 pages, dated Apr. 9, 2020. [with English Translation.].

(Continued)

*Primary Examiner* — Betelhem Shewareged
(74) *Attorney, Agent, or Firm* — Viksnins Harris Padys Malen LLP

(57) ABSTRACT

The present invention relates to a patterned substrate comprising first regions having first dendrimer structures and second regions having second dendrimer structures on a surface of the substrate, as well as a to method for manufacturing a patterned substrate and the use of a patterned substrate for the chemical synthesis of a chemical synthesis product, as a characterizing platform and/or as a platform for cell treatment and/or cell cultivation.

20 Claims, 11 Drawing Sheets

(56) References Cited

U.S. PATENT DOCUMENTS

Figure 1:
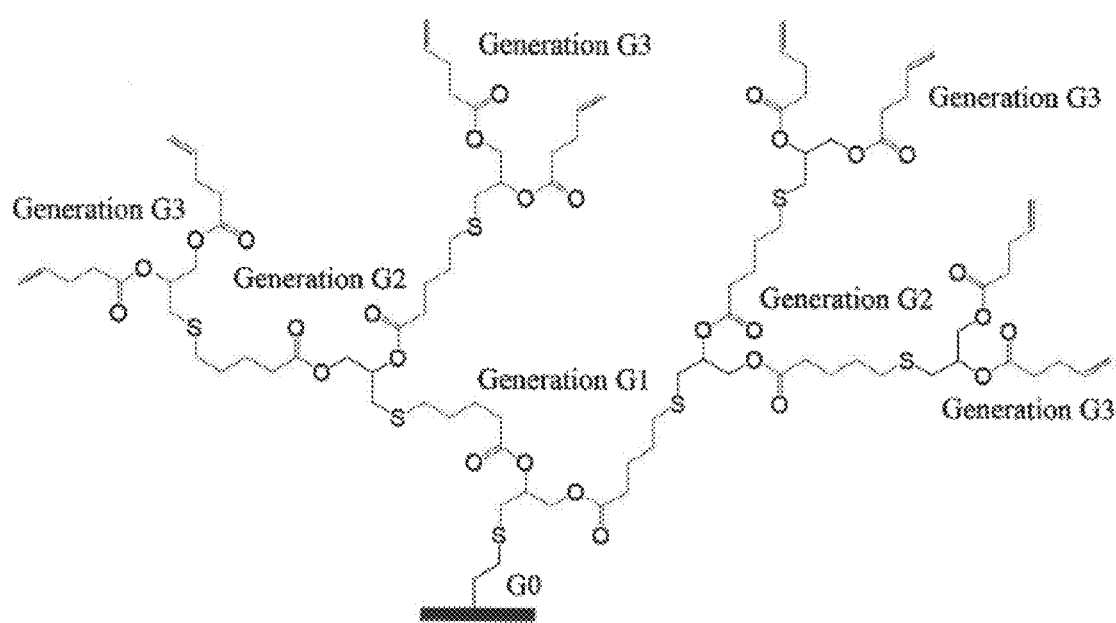

| | | | |
|---|---|---|---|
| 2013/0145488 A1* | 6/2013 | Wang | C12N 15/895 |
| | | | 435/459 |
| 2014/0186770 A1 | 7/2014 | Aqad et al. | |
| 2015/0118624 A1 | 4/2015 | Nakasugi et al. | |
| 2017/0363953 A1 | 12/2017 | Steinhart et al. | |
| 2018/0059550 A1 | 3/2018 | Mirkin et al. | |
| 2019/0023842 A1 | 1/2019 | Kobayashi et al. | |
| 2019/0316223 A1* | 10/2019 | Bihel | A61K 49/226 |
| 2022/0119750 A1* | 4/2022 | Benz | C08G 83/002 |

OTHER PUBLICATIONS

Caminade, A., et al., "Uses of Dendrimers for DNA Microarrays", Sensors 6, 901-914 (2006).

Kim, M., et al., "Designing culture surfaces based on cell anchoring mechanisms to regulate cell morphologies and functions", Biotechnology Advances 28, 7-16 (2010).

* cited by examiner

PATTERNED, DENDRIMERIC SUBSTRATE SURFACES AND PRODUCTION AND USE THEREOF

CROSS-REFERENCE TO RELATED APPLICATION(S)

This application claims the benefit of priority of DE Application No. 10 2019 001 137.6, filed Feb. 15, 2019.

The present invention relates to a patterned substrate comprising first regions having first dendrimer structures and second regions having second dendrimer structures on a surface of the substrate, as well as to a method for manufacturing a patterned substrate and the use of a patterned substrate for the chemical synthesis of a chemical synthesis product, as a characterizing platform and/or as a platform for cell treatment and/or cell cultivation.

The development of new active ingredients and biologically interesting molecules is a time- and resources-consuming process. First, thousands of new compounds have to be prepared and characterized individually before they can be examined in high-throughput screenings with regard to their biological activity and properties. In this case, all steps of this molecule development are carried out separately both with regard to time and space.

First, in the chemical synthesis thousands of compounds have to be synthesized individually and one after the other in order to build a primary molecular library. Usually, the synthesis is carried out in round bottom flasks, wherein reagents are often used in a milliliter/milligram-scale. In this case, the classic organic synthesis is carried out in solution, wherein almost always organic solvents (inter alia ethanol, acetone, dichloromethane (DCM), dimethylformamide (DMF), dimethylsulfoxide (DMSO), etc.) are used. Subsequently, all products have to be characterized in order to be able to evaluate the success of the synthesis. Although small amounts of the compound are frequently sufficient for this purpose, the focus in the transition between chemical synthesis and characterization is, however, the method of characterization and the device-specific facilities associated therewith.

The method of choice for characterizing large molecular libraries is the matrix-assisted laser desorption/ionization with time-of-flight analysis (MALDI-TOF) mass spectrometry (MS). On the one hand, MALDI-TOF MS merely requires a very small amount of sample substance, and it is on the other hand a very fast method, which can be simply automated, by which large molecular libraries can be characterized within a very short time.

However, MALDI-TOF MS requires a specific platform, the surface of which is electrically conductive. Thus, initially all compounds of the molecular library synthesized beforehand have to be individually transferred onto the MALDI-TOF platform one after the other. During this time-consuming process, an immense amount of expendable materials is produced, such as pipet tips (per compound one tip for transferring the compound and a further one for applying matrix solution necessary for analysis).

A still larger challenge is the subsequent cell-biological screening. While the molecular library can be prepared under harsh conditions (high temperatures, organic solvents, protective gas atmosphere, etc.), cell experiments may be carried out merely under very mild conditions (room temperature, aqueous solvents, oxygen-carbon dioxide atmosphere, etc.).

Due to the spatial and temporal separation and due to the immense effort concerning personnel, chemicals, solvents, cell suspension and other expendable materials, the time frame for developing a single new medicament is frequently more than 20 years and consumes a budget of more than 800 million US dollars. A combination of different operational procedures, such as the synthesis of compounds of the molecular library and their characterization and cell-biological screening, could shorten this time frame and result in a reduction of costs.

In principle, a synthesis could be carried out in a miniaturized design, such as in a microarray system. Basically, there are two different kinds of microarrays, which differ with regard to the type of patterned surfaces and which may be selected accordingly by a skilled person according to the solvent to be used. For aqueous solvents having a high surface tension (more than $72.2$ mN·m$^{-1}$) high surface tension liquids (HSTL) microarrays are generally used, whereas for organic solvents having a lower surface tension (less than $72.2$ mN·m$^{-1}$) low surface tension liquids (LSTL) microarrays are used. However, it is not possible to use one of these array for the respective other solvents.

Furthermore, up to now it was not possible to carry out both a combinatorial synthesis in a liquid phase and the characterization by, for example, MALDI-TOF MS, and a biological screening in a droplet array format on a single substrate in a direct sequence.

Thus, it is the object of the present invention to provide a substrate which allows both to carry out a combinatorial synthesis in a liquid phase and the characterization by, for example, MALDI-TOF MS, and a biological screening in a droplet array format on the same in a direct sequence and to allow different solvents, in particular solvents having different surface tensions.

This object is achieved by the embodiments characterized in the claims.

In particular, the present invention relates to a patterned substrate comprising first regions and second regions on a surface of the substrate, wherein the first regions have first dendrimer structures and the second regions have second dendrimer structures; the dendrimer structures are each covalently connected with the substrate surface; the second regions enclose the first regions; and the second dendrimer structures have at least one structural element different from the structural elements of the first dendrimer structures.

The substrate according to the invention advantageously allows to provide a flat platform, on which preferably clearly defined and delimited droplets both with organic solvents having a lower surface tension for, for example, an organic liquid phase synthesis, and with aqueous solvents having a high surface tension for, for example, biological high-throughput screenings in an array format may be produced. By the substrate according to the invention it is preferably further possible to both carry out a combinatorial synthesis in an aqueous phase and the characterization by, for example, MALDI-TOF MS and a biological screening in a droplet array format on a single substrate in a direct sequence.

In particular, the substrate according to the invention preferably has a surface texture compatible for MALDI-TOF MS and does not have any limitations concerning the chemical synthesis process (with regard to surface stability) and the biological application (with regard to cell compatibility) in this context.

By combining, miniaturizing and parallelizing of all regions of the early phase of developing a medicament (synthesis, characterization and screening of large molecular libraries) on a single substrate, the substrate according to the invention preferably allows a considerable improvement of efficiency in the development of new, biologically interesting compounds, however, on the other hand, also preferably allows a drastic reduction of costs of this development compared to existing methods.

According to the invention, the substrate is patterned, i.e., has a patterned surface layer. The patterned surface layer is formed by the first regions and the second regions on at least one surface of the substrate, wherein the second regions enclose the first regions (parallel to the substrate surface). The material of the substrate is not particularly limited, as long as the substrate has a surface having hydroxyl groups or silanol groups. Such a substrate may be provided directly or, for example, also by applying a coating having hydroxyl groups or silanol groups on a base material without hydroxyl groups. Preferably, the substrate comprises metals having an oxidized surface, such as aluminum, preferably an aluminum foil, semiconductor materials, glass, silicon dioxide, silicon dioxide nanoparticles, indium oxide, tin oxide, mixed oxides, silicone, polydimethylsiloxane (PDMS) or an organic polymer having surface hydroxyl groups, such as poly(2-hydroxyethylmethacrylate-co-ethylenedimethacrylate) (HEMA-EDMA copolymer).

In a preferred embodiment, the patterned substrate has a flat surface. Although the shape of the substrate is not particularly limited, preferably the substrate has the shape of a (specimen) holder or plate, a sheet metal, a layer, a coating or a film, still more preferably of a (specimen) holder or plate (coated or non-coated). In this context, the term "film" both comprises self-supporting films and films applied on another substrate. In a preferred embodiment of the present application, the substrate has a surface which is independently selected from the group consisting of a glass surface, semiconductor materials (such as a silicon wafer and indium-tin oxide (ITO)), a flat plastic film, a metal oxide surface and a metal surface. Preferably, the surface of the substrate having the first and second regions has an electrically conductive material or is consisting thereof. Preferably, the substrate has a surface of indium-tin oxide. Particularly preferable the substrate is an indium-tin oxide-coated glass. The patterning of such a surface preferably maintains the electric conductivity of the surface. A correspondingly patterned substrate is particularly advantageous in view of the applicability in a substance synthesis as well as in a direct characterization of the substances, for example, by MALDI-TOF MS.

According to the invention, the patterned substrate comprises first regions and second regions on a surface of the substrate. With regard to their shape, the first regions and second regions are not particularly limited. The first regions may be circular, star-shaped or polygonal (triangular, rectangular, pentagonal, hexagonal, . . . ) and the second regions enclose the same correspondingly. First regions having a triangular or rectangular shape allow a close arrangement of the first regions on the substrate. Preferably, the first and second regions form a microarray.

Due to its specific surface patterning, the patterned substrate according to the invention is able to carry at least one drop of a solution on this patterned surface. In a preferred embodiment, a patterned substrate is suitable to carry at least 1 drop per cm$^2$ of the patterned surface, more preferably at least 4 drops per cm$^2$ of the patterned surface, still more preferably at least 8 drops per cm$^2$ of the patterned surface, and most preferably at least 16 drops per cm$^2$ of the patterned surface. The upper limit of the number of drops per cm$^2$ of the patterned surface is not particularly limited and may be determined according to the requirements. Corresponding drops, which may be arranged on the patterned surface of a patterned substrate, have, for example, a volume from 100 pL to 1 mL, preferably from 1 nL to 100 μL, still more preferably from 100 nL to 50 μL and most preferably from 500 nL to 25 μL.

The first regions may, for example, be triangular or rectangular and have a lateral length of 5.0 mm or less, 3.0 mm or less, 1.0 mm or less or 500 μm or less. In a preferred embodiment of the present invention, the first regions are circular and have a diameter of 5.0 mm or less, more preferably 3.0 mm or less, still more preferably 1.0 mm or less. The second regions enclosing the first regions preferably have a width of 2.0 mm or less, more preferably 1.0 mm or less and most preferably 0.5 mm or less.

According to the invention, the first regions have first dendrimer structures and the second regions have second dendrimer structures. In this context, the term "dendrimer structures" refers to structures, which branch starting from a core (see FIG. 1). The dendrimer structures have branches of repeating units. The repeating units each have independently from each other at least two branching points, preferably two to five branching points, still more preferably two to four branching points, still more preferably two or three branching points and most preferably two branching points. The dendrimer structures have at least two generations of repeating units, i.e., starting from the core the dendrimer structures have at least two successive repeating units (per main branch). Preferably, the dendrimer structures each have independently from each other two to five, still more preferably two to four, still more preferably two or three, and most preferably three generations of repeating units.

According to the invention, the dendrimer structures each are covalently attached to the substrate surface. Thus, the core of the dendrimer structures is covalently attached to the substrate surface. The dendrimer structures have terminal groups at their ends. The terminal groups may correspond to the last generation of repeating units or may be different structural elements (including partial structures of the repeating units) being linked to the last generation of repeating units.

According to the invention, the second dendrimer structures have at least one structural element, which is different from the structural elements of the first dendrimer structures. The same may be the repeating units, the core and/or the terminal groups of the dendrimer structures. Preferably, the first and second dendrimer structures in the terminal groups are different, particularly preferable only in the terminal groups.

By the different structural element, it is preferably possible to form such different first and second regions such that in the first regions respective clearly defined droplets, which are clearly delimited from each other, may form both with organic solvents having a low surface tension for an organic liquid-phase synthesis and with aqueous solvents having a high surface tension. In this case, the first regions are delimited from each other by the second regions surrounding them. Preferably, the first regions are hydrophilic, still more preferably hydrophilic and omniphilic, and the second regions are hydrophobic, still more preferably hydrophobic and omniphobic.

In general, surfaces may be classified to be hydrophilic or hydrophobic depending on their contact angle with water. In this context, a surface having a static contact angle of at least 90° is denoted as hydrophobic, whereas a surface having a static contact angle of less than 90° is denoted as hydrophilic. Usually, it is differentiated between two different contact angles: a static and a dynamic contact angle. Static contact angles ($\theta_{stat}$) are determined by applying a drop on a surface and measuring the contact angle of the applied drop at rest with the surface by a goniometer or a camera having a specific software (sessile drop measurement). In contrast, dynamic contact angles represent contact angles beyond a state of equilibrium and are measured during advancing ($\theta_{adv}$) or receding ($\theta_{rec}$) of a drop. The difference between $\theta_{adv}$ and $\theta_{rec}$ is denoted as contact angle hysteresis.

In a preferred embodiment of the present invention, hydrophobic regions, preferably the second regions, have a static water contact angle of at least 90°, preferably more than 95°, still more preferably more than 100°, still more preferably more than 105° and most preferably more than 110°. Preferably, hydrophobic regions, preferably the second regions, have a water receding contact angle ($\theta_{rec}$) of at least 70°, preferably more than 80°, still more preferably more than 90°, still more preferably more than 100° and most preferably more than 105°. A water advancing contact angle ($\theta_{adv}$) of a hydrophobic region, preferably the second regions, preferably is at least 100°, preferably more than 105°, still more preferably more than 110°, still more preferably more than 115° and most preferably more than 120°.

Preferably, hydrophilic regions, preferably the first regions, have a static water contact angle of less than 90°, preferably less than 70°, still more preferably less than 60°, still more preferably less than 50°, still more preferably less than 40° and most preferably less than 30°.

In a preferred embodiment of the present invention, hydrophilic regions, preferably the first regions, have a water receding contact angle ($\theta_{rec}$) of at most 60°, preferably less than 30°, still more preferably less than 20°, still more preferably less than 15° and most preferably less than 10°. A water advancing contact angle ($\theta_{adv}$) of a hydrophilic region, preferably the first regions, preferably is at most 80°, preferably less than 65°, still more preferably less than 50°, still more preferably less than 45° and most preferably less than 40°.

In general, depending on their contact angles with aqueous and organic liquids, surfaces may be classified as omniphilic or omniphobic. In this context, a surface having a static contact angle of at least 90° is denoted as omniphobic, while a surface having a static contact angle of less than 90° is denoted as omniphilic. The terms "omniphilic" and "omniphobic" relate to aqueous and organic solutions.

Unless otherwise noted, the following definitions apply with regard to the terms "halogen", "alkyl group", "cycloalkyl group", "aryl group" and "heteroaryl group". In particular, the term "halogen" denotes fluorine atoms, chlorine atoms and bromine atoms. Furthermore, the term "alkyl group" denotes a branched or linear alkyl group having 1 to 20, preferably 1 to 12, still more preferably 1 to 6 carbon atoms, wherein the alkyl group may be substituted or unsubstituted. The term "cycloalkyl group" denotes a cycloalkyl group having 3 to 10, preferably 4 to 8, still more preferably 5 or 6 carbon atoms, wherein the cycloalkyl group may be substituted or unsubstituted. The term "aryl group" denotes an aryl group consisting of, for example, 1 to 3 aromatic rings, such as a phenyl group or a naphthyl group, wherein the aryl group may be substituted or unsubstituted. The term "heteroaryl group" denotes a heteroaryl group consisting of, for example, 1 to 3 aromatic rings having hetero atoms, such as a pyridyl group, a pyrimidinyl group, a thienyl group, a furyl group or a pyrrolyl group, wherein the heteroaryl group may be substituted or unsubstituted.

As described above, the alkyl group, the cycloalkyl group, the aryl group, and the heteroaryl group may be substituted or unsubstituted. Furthermore, in the general formulae indicated herein, unless otherwise noted, the chain carbon atoms may be substituted or unsubstituted. The possible substituents are not particularly limited, i.e., instead of hydrogen atoms any substituents known in the prior art may be attached at the further positions of the corresponding group. For example, the possible substituents are selected from the group consisting of a branched or linear alkyl group having 1 to 6 carbon atoms, a cycloalkyl group having 4 to 8 carbon atoms, an aryl group having 1 to 3 aromatic rings, a heteroaryl group having 1 to 3 aromatic rings having hetero atoms, $-NL^1L^2$, $-NO_2$, $-CN$, $-OP$, $-C(O)L^4$, $-C(O)NL^5L^6$, $-COOL^7$ and $-SO_3L^8$, wherein $L^1$ to $L^8$ are independently selected from the group consisting of hydrogen, a branched or linear alkyl group having 1 to 6 carbon atoms, a cycloalkyl group having 4 to 8 carbon atoms, an aryl group having 1 to 3 aromatic rings, a heteroaryl group having 1 to 3 aromatic rings having hetero atoms.

Preferably, the possible substituents are selected from the group consisting of a branched or linear alkyl group having 1 to 6 carbon atoms, an aryl group having 1 to 3 aromatic rings, a heteroaryl group having 1 to 3 aromatic rings having hetero atoms, $-NH_2$, $-NHCH_3$, $-N(CH_3)_2$, $-NO_2$, $-OH$, $-OCH_3$, $-OEt$, $-C(O)H$, and $-COOH$. Furthermore, one or more tetravalent carbon atoms (together with the hydrogen atoms attached thereto), if present, in the alkyl groups and cycloalkyl groups may be independently from each other substituted with a member selected from the group consisting of O, $(OCH_2CH_2)_aO$, S, $(SCH_2CH_2)_bS$, C(O), C(O)O, $NL^9$ and $C(O)NL^{10}$, preferably consisting of O, $(OCH_2CH_2)_aO$, C(O)O and $C(O)NL^{10}$, wherein a and b independently from each other are an integer from 1 to 6. $L^9$ and $L^{10}$ are independently from each other selected from the group consisting of hydrogen, a branched or linear alkyl group having 1 to 6 carbon atoms, a cycloalkyl group having 4 to 8 carbon atoms, an aryl group having 1 to 3 aromatic rings, a heteroaryl group having 1 to 3 aromatic rings having hetero atoms.

Preferably, the alkyl group, the cycloalkyl group, the aryl group, and the heteroaryl group are unsubstituted. Preferably, the alkyl group is non-branched. Preferably, the chain carbon atoms in the general formulae disclosed herein may be substituted or unsubstituted.

In a preferred embodiment of the present invention, the (first and second) dendrimer structures each have an alkylene silyl group, and the dendrimer structures are attached to the substrate surface by the respective alkylene silyl group (via the oxygen atoms of the hydroxyl groups or silanol groups of the substrate surface). The alkylene silyl groups may be regarded as a core of the corresponding preferable dendrimer structures. Preferably, the silicon atoms are attached to the hydroxyl groups or silanol groups of the substrate surface via $-Si-O$ bonds and the alkylene moieties to the repeating units, as exemplary shown in FIG. 1 (the silicon atom is not shown). The alkylene silyl groups of the first and second dendrimer structures may be the same or different. Preferably, the alkylene silyl groups are the same, since in this case the synthesis effort can be kept low.

Preferably, the alkylene silyl group (the first and/or second dendrimer structures) has a structure having the following general formula (1), which may be substituted or unsubstituted, Formula (1)

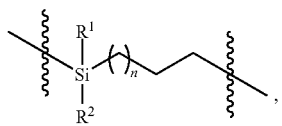

wherein $R^1$ and $R^2$ are independently selected from the group consisting of an alkyl group, a cycloalkyl group, an aryl group, a heteroaryl group, -OA, wherein A is independently from each other selected from the group consisting of an alkyl group, a cycloalkyl group, an aryl group, and a heteroaryl group; and n is an integer from 0 to 6. Preferably, A is an alkyl group or an aryl group, still more preferably A is an alkyl group, for example, an alkyl group having 1 to 6 carbon atoms, preferably having 1 or 2 carbon atoms. Still more preferably, A is an ethyl group. Preferably, $R^1$ and $R^2$ are independently from each other an alkyl group, an aryl group or -OA, still more preferably an alkyl group or -OA and still more preferably -OA. $R^1$ and $R^2$ each are, for example, a methyl group, a methoxy group or an ethoxy group, preferably each a methoxy group or an ethoxy group, still more preferably each an ethoxy group. Preferably, n is an integer from 0 to 4, still more preferably from 0 to 2 and still more preferably of 0 or 1 and most preferably n is 0. The alkylene silyl group preferably has a structure having the following general formula (1a) or (1b), most preferably a structure having the following general formula (1 b).

Formula (1a)

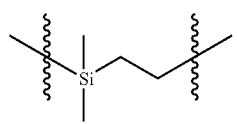

Formula (1b)

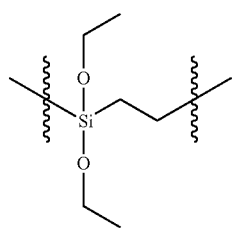

In a preferred embodiment of the present invention, the first dendrimer structures and the second dendrimer structures each have repeating units having the following general formula (2) or (3), which may be substituted or unsubstituted, preferably respective repeating units having the following general formula (2), Formula (2)

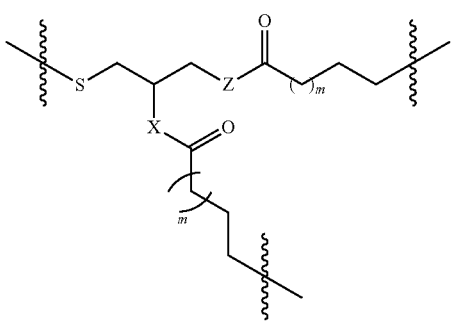

Formula (3)

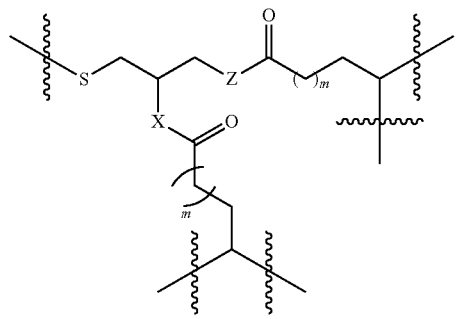

wherein X and Z are independently from each other $NR^3$ or O, wherein each $R^3$ is independently from each other selected from the group consisting of hydrogen, an alkyl group, a cycloalkyl group, an aryl group, and a heteroaryl group; and m is an integer from at least 1. Preferably, $R^3$ is hydrogen or an alkyl group, still more preferably hydrogen. In a preferred embodiment, X and Z each are O. Preferably, m is an integer from 1 to 6, still more preferably from 1 to 4, still more preferably of 1 or 2 and most preferably m is 1. Preferably, the first dendrimer structures and the second dendrimer structures each have repeating units having the following general formula (2a) or (3a), still more preferably each have repeating units having the following general formula (2a).

Formula (2a)

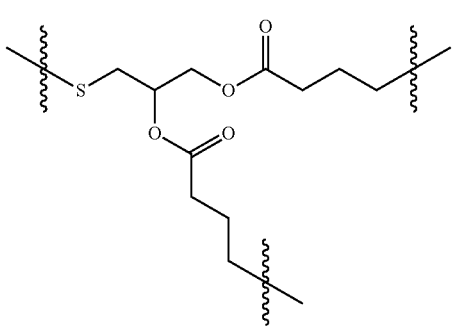

Formula (3a)

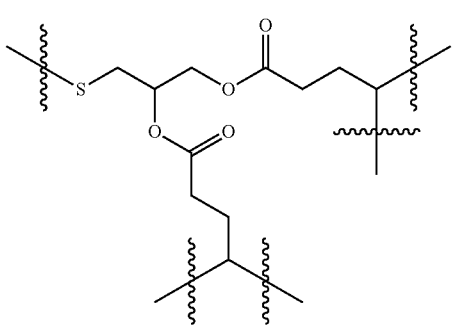

The first dendrimer structures preferably have terminal groups having the following general formula (4) or (5), which may be substituted or unsubstituted, preferably a terminal group having the following general formula (4).

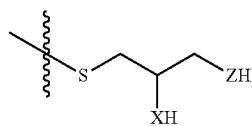

Formula (4)

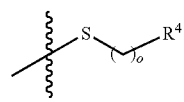

Formula (5)

For X and Z in the general formula (4) the above definitions and embodiments with respect to X and Z of the repeating units having the general formula (2) or (3) apply in an analogous manner. Preferably, the terminal groups having the general formula (4) have the following formula (4a).

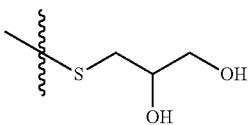

Formula (4a)

In the general formula (5) $R^4$ is selected from the group consisting of $-NG^1G^2$, $-NO_2$, $-CN$, $-OG^3$, $-C(O)G^4$, $-C(O)NG^5G^6$, $-COOG^7$, and $-SO_3G^8$, wherein $G^1$ to $G^8$ are independently from each other selected from the group consisting of hydrogen, an alkyl group, a cycloalkyl group, an aryl group, and a heteroaryl group. Preferably, $G^1$ to $G^8$ are independently from each other hydrogen or an alkyl group, still more preferably hydrogen. In a preferred embodiment, $R^4$ is $-NG^1G^2$ or $-OG^3$, still more preferably $-NG^1G^2$, and most preferably $-NH_2$. Furthermore, in the general formula (5) o is an integer from 1 to 6. Preferably, o is an integer from 1 to 4 and still more preferably from 2 or 3, and most preferably o is 2. In a preferred embodiment, the terminal groups having the general formula (5) have the following formula (5a).

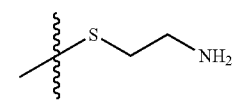

Formula (5a)

The first dendrimer structures most preferably have terminal groups having the general formula (4a).

The second dendrimer structures preferably have terminal groups having the following general formula (6), which may be substituted or unsubstituted,

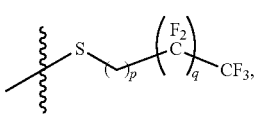

Formula (6)

wherein p is an integer from 0 to 10 and q is an integer from 3 to 15. Preferably, p is an integer from 0 to 6, and still more preferably from 1 to 3, and most preferably p is 2. Furthermore, q is preferably an integer from 4 to 12, still more preferably from 5 to 9, and still more preferably from 6 to 8, and most preferably q is 7. Most preferably, the second dendrimer structures have terminal groups having the following general formula (6a).

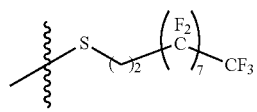

Formula (6a)

In a particularly preferred embodiment of the present invention, the first and second dendrimer structures each have an alkylene silyl group having a structure having the general formula (1b) and respective three (consecutive) repeating units having the general formula (2a), the first dendrimer structures have terminal groups having the general formula (4a) and the second dendrimer structures have terminal groups having the general formula (6a). Corresponding dendrimer structures (before introducing the terminal groups) are exemplary shown in FIG. 1 (silicon atoms of the alkylene silyl group are not shown).

A further aspect of the present invention particularly relates to a method for manufacturing a patterned substrate according to the invention, comprising applying second dendrimer structures in second regions and first dendrimer structures in first regions on a surface of the substrate, wherein the dendrimer structures each are covalently connected with the substrate surface; the second regions enclose the first regions; and the second dendrimer structures have at least one structural element different from the structural elements of the first dendrimer structures. The above definitions and embodiments apply to this aspect of the present invention in an analogous manner.

Preferably, the method of manufacturing according to the invention comprises the steps of (a) providing a substrate comprising a surface having hydroxyl groups or silanol groups;

(b) reacting the hydroxyl groups or silanol groups of this surface with an alkenyl silane having the following general formula (12) to form alkenyl silyl groups on the surface

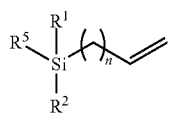

Formula (12)

wherein $R^1$ and $R^2$ are independently selected from the group consisting of an alkyl group, a cycloalkyl group, an aryl group, a heteroaryl group, -OA, wherein A independently from each other is independently selected from the group consisting of an alkyl group, a cycloalkyl group, an aryl group, and a heteroaryl group;

$R^5$ is a halogen or -OQ, wherein Q is independently selected from the group consisting of an alkyl group, a cycloalkyl group, an aryl group, and a heteroaryl group; and n is an integer from 0 to 6;

(c) reacting with a thiol compound having the following general formula (7)

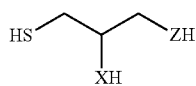
Formula (7)

wherein X and Z are independently from each other NR³ or O, wherein each R³ is independently from each other selected from the group consisting of hydrogen, an alkyl group, a cycloalkyl group, an aryl group, and a heteroaryl group;

(d) reacting with a carboxylic acid having the following general formula (8) or (9)

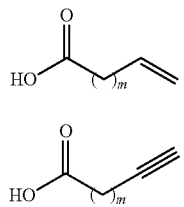
Formula (8)

Formula (9)

wherein m is an integer of at least 1;

(e) at least 1 time repeating the steps (c) and (d) in combination;

(f) selective reacting a part of the alkenyl or alkynyl groups obtained from the last performing of step (d), either with
(i) a thiol compound having the following general formula (10) to obtain second dendrimer structures

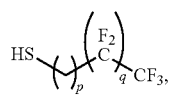
Formula (10)

wherein p is an integer from 0 to 10, and q is an integer from 3 to 15; or with
(ii) a thiol compound having the general formula (7) or a thiol compound having the following general formula (11) to obtain first dendrimer structures

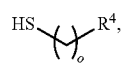
Formula (11)

wherein R⁴ is selected from the group consisting of -NG¹G², —NO₂, —CN, -OG³, —C(O)G⁴, —C(O)NG⁵G⁶, -COOG⁷, and —SO₃G⁸, wherein G¹ to G⁸ are independently selected from the group consisting of hydrogen, an alkyl group, a cycloalkyl group, an aryl group, and a heteroaryl group; and
is an integer from 1 to 6;

(g) reacting the remaining alkenyl or alkynyl groups either with
(i) a thiol compound having the general formula (7) or a thiol compound having the general formula (11) to obtain first dendrimer structures in case in step (f) second dendrimer structures have been formed (according to (i) in step (f)); or with
(ii) a thiol compound having the general formula (10) to form second dendrimer structures in case in step (f) first dendrimer structures have been formed (according to (ii) in step (f)).

In a preferred embodiment, step (a) comprises step (al) of activating the surface of the substrate. The means for activating are not particularly limited. For example, the substrate surface may be activated by plasma treatment or a consecutive treatment with NaOH and HCl, preferably by plasma treatment. The plasma treatment may be carried out, for example, for 1 min to 2 hours, preferably for 2 min to 40 min and most preferably for 5 min to 15 min, at, for example, from 0 to 80° C., preferably from 15 to 40° C., and most preferably from 20 to 30° C.

In step (b) the hydroxyl groups or silanol groups of the surface of the substrate are reacted with an alkenyl silane having the general formula (12), which may be substituted or unsubstituted, to form alkenyl silyl groups on the surface. The first and second dendrimer structures may be connected with the substrate surfaces via said alkylene silyl groups. For R¹, R², and n in the general formula (12) the above definitions and embodiments with respect to R¹, R², and n of the structure having the general formula (1) apply in an analogous manner. R⁵ is a halogen or -OQ, wherein Q is independently selected from the group consisting of an alkyl group, a cycloalkyl group, an aryl group, and a heteroaryl group. The halogen of the group R⁵ may, for example, be chlorine, bromine, or iodine. Preferably, the halogen is chlorine. Preferably, Q is an alkyl group or an aryl group, still more preferably Q is an alkyl group, for example, an alkyl group having 1 to 6 carbon atoms, preferably having 1 or 2 carbon atoms. Still more preferably, Q is an ethyl group. R⁵ preferably is -OQ, still more preferably -OQ is an ethoxy group. The alkenyl silane is preferably chloro(dimethyl)vinylsilane or triethoxyvinylsilane, most preferably triethoxyvinylsilane.

The (reaction) temperature in step (b) is not particularly limited. Thus, the skilled person may use common temperatures. In a preferred embodiment, the (reaction) temperature in step (b) is from 10 to 150° C., still more preferably from 30 to 120° C., still more preferably from 50 to 100° C., still more preferably from 70 to 90° C. and most preferably 80° C.

The (reaction) time in step (b) is not particularly limited. Thus, the skilled person may use common durations. In a preferred embodiment, the (reaction) time in step (b) is from 30 min to 48 hours, still more preferably from 2 hours to 36 hours, still more preferably from 6 hours to 24 hours and most preferably from 10 hours to 14 hours.

The reaction in step (b) may be carried out by applying a solution of the alkenyl silane onto the surface of the substrate or by a reaction in the gas phase. Preferably, the reaction is carried out in the gas phase. Preferably, the reaction in the gas phase is carried out under reduced pressure. In this context, for example, a pressure of 1 mbar to 800 mbar, preferably from 10 mbar to 400 mbar, still more preferably from 20 mbar to 200 mbar and most preferably from 30 mbar to 100 mbar may be applied.

In steps (c) and (d) the repeating units of the dendrimer structures are formed. Per carrying out the combination of the steps (c) and (d), one generation of repeating units is obtained.

In step (c), reacting with a thiol compound having the general formula (7), which may be substituted or unsubstituted, is carried out. For X and Z in the general formula (7)

the above definitions and embodiments with respect to X and Z of the repeating units having the general formula (2) or (3) apply in an analogous manner. Preferably, the thiol compound having the general formula (7) is thioglycerol having the following formula (7a).

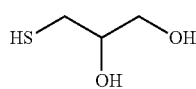

Formula (7a)

When step (c) is carried out for the first time, the alkenyl groups of the alkenyl silane from step (b) are reacted with the thiol compound having the general formula (7). When step (c) is carried out further, the alkenyl or alkynyl groups of the carboxylic acids from step (d) carried out before are reacted. Corresponding reactions are known from the prior art. Preferably, the reaction is carried out by thiol-ene-click and thiol-yne-click reactions, respectively.

The reaction in step (c) is not particularly limited. For example, it may be thiol-ene-click and thiol-yne-click reactions, respectively. In a preferred embodiment, the reaction in step (c) is carried out by a photoreaction, i.e., stimulated by light, preferably with UV light. The light source is not particularly limited. For example, it may be irradiated with light having a wavelength from 200 to 360 nm, preferably 260 nm, at an intensity of 0.5 to 20 mW·cm$^{-2}$, preferably from 2 to 5 mW·cm$^{-2}$. Light emitted from the light source may initiate the reaction or may be used to excite an optional photoinitiator having an absorption range in the wavelength range of the light emitted from the light source.

In a preferred embodiment of the method according to the invention, step (c) may be carried out in the presence of a photoinitiator, such as 2,2-dimethoxy-2-phenylacetophenone (DMPAP), which after light absorption decomposes to reactive species initiating further reactions. The photoinitiator may, for example, be present in a concentration from 1.0 to 30 mg·mL$^{-1}$, in particular from 1.0 to 20 mg·mL$^{-1}$, and most preferably from 5.0 to 15 mg·mL$^{-1}$ besides the thiol compound having the general formula (7). The photoinitiator may be applied together with the thiol compound having the general formula (7).

The (reaction) temperature in step (c) is not particularly limited. Thus, the skilled person may use common temperatures. In a preferred embodiment, the (reaction) temperature in step (c) is from 0 to 80° C., still more preferably from 10 to 60° C., still more preferably from 15 to 40° C., and most preferably from 20 to 30° C.

The (reaction) time in step (c) is not particularly limited. Thus, the skilled person may use common durations. In a preferred embodiment, the (reaction) time in step (c) is from 10 s to 40 min, still more preferably from 30 s to 15 min, and most preferably from 1 min to 3 min.

The reaction in step (c) may be carried out by applying the thiol compound having the general formula (7) or a solution thereof onto the surface of the substrate. Preferably, the reaction with a solution of the thiol compound having the general formula (7) is, for example, carried out with a 1 to 40 vol % solution, preferably a 5 to 20 vol % solution and most preferably a 10 vol % solution. The reaction medium (medium) for step (c) is not particularly limited. For example, the medium may be an aqueous medium, a medium based on one or more organic solvents or a medium based on a mixture of water and one or more organic solvents. Preferably, the reaction medium for step (c) of the method of manufacturing according to the invention is selected from the group consisting of water, ethanol, methanol, isopropanol and acetone. Most preferably, the reaction medium for step (c) of the method of manufacturing according to the invention is a mixture of water and ethanol, preferably in a volume ratio of 1:1.

In step (d), the reaction with a carboxylic acid having the general formula (8) or (9), which may be substituted or unsubstituted, is preferably carried out with a carboxylic acid having the general formula (8). For m in the general formulae (8) and (9) the above definitions and embodiments with respect to m of the repeating units having the general formula (2) or (3) apply in an analogous manner. Preferably, the carboxylic acid having the general formula (8) is 4-pentenoic acid and the carboxylic acid having the general formula (9) is 4-pentynoic acid. In step (d), the functional groups XH and ZH, which are present due to the reaction with the thiol compound having the general formula (7) in step (c), are reacted with the carboxylic acid in step (d), such that (together with step (c)) a (further) generation of the repeating unit is obtained.

The reaction in step (d) is not particularly limited. For example, the substrate from step (c) may be treated with a solution containing the carboxylic acid having the general formula (8) or (9), for example, by immersing the substrate into the solution.

In a preferred embodiment of the method of manufacturing according to the invention step (d) is carried out in the presence of a nucleophilic catalyst, such as 4-(dimethylamino)pyridine (DMAP). The nucleophilic catalyst may, for example, be present in a concentration from 0.1 to 50 mg·mL$^{-1}$, in particular from 1.0 to 10 mg·mL$^{-1}$, and most preferably from 1.0 to 5.0 mg·mL$^{-1}$ besides the carboxylic acid.

Preferably, step (d) is carried out in the presence of a coupling reagent, such as N,N'-diisopropyl carbodiimide (DIC) or dicyclohexyl carbodiimide (DCC), preferably N,N'-diisopropyl carbodiimide (DIC). The coupling reagent may be present, for example, in a concentration of 0.1 to 1.0 vol %, in particular from 0.1 to 0.5 vol %, and most preferably from 0.1 to 0.3 vol % besides the carboxylic acid.

The (reaction) temperature in step (d) is not particularly limited. Thus, the skilled person may use common temperatures. In a preferred embodiment, the (reaction) temperature in step (d) is from −40 to 60° C., still more preferably from −20 to 50° C., still more preferably from 10 to 40° C., and most preferably from 20 to 30° C.

The (reaction) time in step (d) is not particularly limited. Thus, the skilled person may use common durations. In a preferred embodiment, the (reaction) time in step (d) is from 30 min to 24 hours, still more preferably from 1 hour to 12 hours, still more preferably from 2 hours to 8 hours, and most preferably from 3 hours to 5 hours.

Preferably, the reaction in step (d) is carried out with a solution of the carboxylic acid having the general formula (8) or (9). The carboxylic acid having the general formula (8) or (9) may be present, for example, in a concentration of 1.0 to 50 mg·mL$^{-1}$, in particular from 1.0 to 20 mg·mL$^{-1}$, and most preferably from 1.0 to 5.0 mg·mL$^{-1}$. The reaction medium (medium) for step (d) is not particularly limited. For example, the medium may be an aqueous medium, a medium based on one or more organic solvents or a medium based on a mixture of water and one or more organic solvents. Preferably, the reaction medium for step (d) of the method of manufacturing according to the invention is selected from the group consisting of acetone and dichloromethane (DCM). Most preferably, the reaction medium for step (d) of the method of manufacturing according to the invention is acetone.

In step (e), the at least 1 time repeating of the steps (c) and (d) is carried out in combination, i.e., in the method of manufacturing according to the invention the steps (c) and (d) are consecutively carried out at least two times (i.e., c, d, c, d). Thus, at least two generations of repeating units may be formed in the dendrimer structures. The maximum number of iterations is not particularly limited. Preferably, the combination of the steps (c) and (d) is repeated 1 to 5 times, still more preferably 1 to 3 times and most preferably 2 times (i.e., forming three generations of repeating units in the dendrimer structures).

By this dendrimeric surface modification, the reactivity of the surface may be raised with each passing of the cycle. After each passing, the number of reactive double bonds on the surface doubles, for example, when using the thiol compound having the general formula (7) and the carboxylic acid having the general formula (8). The density of functional groups in the same space steadily raises. After the third passing of the cycle, for example, the number may be raised from originally one immobilised double bond to eight double bonds, as shown in FIG. 1.

In step (f), the specific reacting of a part of the alkenyl or alkynyl groups, which were obtained from the final performance of step (d), is carried out. In this context, first either second dendrimer structures (according to (i)) with a thiol compound having the general formula (10), which may be substituted or unsubstituted, are formed, or first dendrimer structures (according to (ii)) with a thiol compound having the general formula (7) or a thiol compound having the general formula (11), preferably with a thiol compound having the general formula (7), which respectively may be substituted or unsubstituted, may be formed. For p and q in the general formula (10), the above definitions and embodiments with respect to p and q of the terminal groups having the general formula (6) apply in an analogous manner. Preferably, the thiol compound having the general formula (10) is 1H,1H,2H,2H-perfluorodecanethiol (PFDT). For X and Z in the general formula (7) the above definitions and embodiments in step (c) apply in an analogous manner. For $R^4$ and o in the general formula (11), the above definitions and embodiments with respect to $R^4$ and o of terminal groups having the general formula (5) apply in an analogous manner. Preferably, the thiol compound having the general formula (11) is cysteamine, most preferably, the thiol compound having the general formula (7) is thioglycerol. The corresponding compounds may also be used as the corresponding salts, such as the corresponding hydrochloride, such as cysteamine-hydrochloride.

In a preferred embodiment, in step (f) the specific reacting of that part of the alkenyl or alkynyl groups, which were obtained from the final performance of step (d), with a thiol compound having the general formula (10), which may be substituted or unsubstituted, is carried out to obtain second dendrimer structures (according to (i)).

The reacting in step (f) is not particularly limited. For example, it may be specific thiol-ene-click or thiol-yne-click reactions using a photomask or a laser beam.

In a preferred embodiment, step (f) comprises the following steps (f1) to (f4):
(f1) applying the corresponding thiol compound onto the surface having alkenyl or alkynyl groups;
(f2) covering the surface with the thiol compound with a photomask;
(f3) irradiating the surface with the thiol compound and the photomask with UV light; and
(f4) removing the photomask.

Step (f) and step (f1), respectively, may be carried out by applying the corresponding thiol compound or a solution thereof onto the surface of the substrate, which has been obtained by carrying out step (d) for the last time. Preferably, the reaction is carried out with a solution of the corresponding thiol compound, for example, a 1 to 40 vol % solution, preferably a 5 to 20 vol % solution and most preferably a 10 vol % solution. The reaction medium (medium) for step (f) is not particularly limited. For example, the medium may be an aqueous medium, a medium based on one or more organic solvents or a medium based on a mixture of water and one or more organic solvents. Preferably, the reaction medium for the reaction according to (i) in step (f) of the method of manufacturing according to the invention is selected from the group consisting of acetone and dichloromethane. Most preferably, the reaction medium for the reaction according to (i) in step (f) of the method of manufacturing according to the invention is acetone. Preferably, the reaction medium for the reaction according to (ii) in step (f) of the method of manufacturing according to the invention is selected from the group consisting of water and ethanol. Most preferably, the reaction medium for the reaction according to (ii) in step (f) of the method of manufacturing according to the invention is a mixture of water and ethanol, preferably in a volume ratio of 1:1.

In a preferred embodiment of the method of manufacturing according to the invention, step (f) is carried out in the presence of a photoinitiator, such as 2,2-dimethoxy-2-phenylacetophenone (DMPAP). In step (f) the photoinitiator may, for example, be present in a concentration of 1.0 to 30 mg·mL$^{-1}$, in particular from 1.0 to 20 mg·mL$^{-1}$, and most preferably from 5.0 to 15 mg·mL$^{-1}$ besides the corresponding thiol compound. The photoinitiator may be applied together with the corresponding thiol compound.

The photomask used in step (f2) is not particularly limited. Thus, the skilled person may use all suitable photomasks known from the prior art. For example, corresponding photomasks have opaque regions having a diameter of preferably 1 nm to 1 cm and light-transmissive regions having a diameter of preferably 1 nm to 1 cm. The size and shape of the opaque regions is not further limited and may be selected by a skilled person corresponding to the desired dimensions of the first and second regions. The light-transmissive and opaque regions are arranged according to the dendrimer structures (first or second), which have to be formed in step (f).

The light source for step (f3) is not particularly limited. The irradiation may be carried out, for example, with light having a wavelength of 200 to 360 nm, preferably 260 nm, at an intensity from 0.5 to 20 mW·cm$^{-2}$, preferably from 2 to 5 mW·cm$^{-2}$.

The (reaction) temperature in step (f) and step (f3), respectively, is not particularly limited. Thus, the skilled person may use common temperatures. In a preferred embodiment, the (reaction) temperature in step (f) and step (f3), respectively, is from 0 to 80° C., still more preferably from 10 to 60° C., still more preferably from 15 to 40° C., and most preferably from 20 to 30° C.

The (reaction) time in step (f) and step (f3), respectively, is not particularly limited. Thus, the skilled person may use common durations. In a preferred embodiment, the (reaction) time in step (f) and step (f3), respectively, is from 10 s to 40 min, still more preferably from 30 s to 15 min, and most preferably from 1 min to 3 min.

In step (g), reacting the remaining alkenyl or alkynyl groups is carried out either with (i) a thiol compound having the general formula (7) or (11), preferably with a thiol compound having the general formula (7), to obtain the first dendrimer structures in case in step (f) second dendrimer structures (according to (i) in step (f)) have been formed; or with (ii) a thiol compound having the general formula (10) to obtain the second dendrimer structures in case in step (f) first dendrimer structures (according to (ii) in step (f)) have been formed. For the thiol compounds the above definitions and embodiments in step (f) apply in an analogous manner. The reaction in step (g) is not particularly limited. For example, it may be thiol-ene-click or thiol-yne-click reactions.

In a preferred embodiment, reacting the remaining alkenyl or alkynyl groups in step (g) is carried out with a thiol compound having the general formula (7) or (11), preferably with a thiol compound having the general formula (7), which may be substituted or unsubstituted, to obtain first dendrimer structures (according to (i)).

In a preferred embodiment, step (g) comprises the following steps (g1) and (g2):

(g1) applying the corresponding thiol compound onto the surface having the remaining alkenyl or alkynyl groups; and (g2) irradiating the surface with the thiol compound with UV light.

Step (g) and step (g1), respectively, may be carried out by applying the corresponding thiol compound or a solution thereof onto the surface of the substrate obtained from step (f). Preferably, the reaction is carried out with a solution of the corresponding thiol compound, for example, a 1 to 40 vol % solution, preferably a 5 to 20 vol % solution and most preferably a 10 vol % solution. The reaction medium (medium) for step (g) is not particularly limited. For example, the medium may be an aqueous medium, a medium based on one or more organic solvents or a medium based on a mixture of water and one or more organic solvents. Preferably, the reaction medium for the reaction according to (i) in step (g) of the method of manufacturing according to the invention is selected from the group consisting of water and ethanol. Most preferably, the reaction medium for the reaction according to (i) in step (g) of the method of manufacturing according to the invention is a mixture of water and ethanol, preferably in a volume ratio of 1:1. Preferably, the reaction medium for the reaction according to (ii) in step (g) of the method of manufacturing according to the invention is selected from the group consisting of acetone and dichloromethane. Most preferably, the reaction medium for the reaction according to (ii) in step (g) of the method of manufacturing according to the invention is acetone.

In a preferred embodiment of the method of manufacturing according to the invention step (g) is carried out in the presence of a photoinitiator, such as 2,2-dimethoxy-2-phenylacetophenone (DMPAP). The photoinitiator may be present in step (g), for example, in a concentration of 1.0 to 30 mg·mL$^{-1}$, in particular from 1.0 to 20 mg·mL$^{-1}$, and most preferably from 5.0 to 15 mg·mL$^{-1}$ besides the corresponding thiol compound. The photoinitiator may be applied together with the corresponding thiol compound.

The light source for step (g2) is not particularly limited. For example, the irradiation may be carried out with light having a wavelength from 200 to 360 nm, preferably 260 nm, at an intensity of 0.5 to 20 mW·cm$^{-2}$, preferably from 2 to 5 mW·cm$^{-2}$.

The (reaction) temperature in step (g) and step (g2), respectively, is not particularly limited. Thus, the skilled person may use common temperatures. In a preferred embodiment, the (reaction) temperature in step (g) and step (g2), respectively, is from 0 to 80° C., still more preferably from 10 to 60° C., still more preferably from 15 to 40° C., and most preferably from 20 to 30° C.

The (reaction) time in step (g) and step (g2), respectively, is not particularly limited. Thus, the skilled person may use common durations. In a preferred embodiment, the (reaction) time in step (g) and step (g2), respectively, is from 10 s to 40 min, still more preferably from 30 s to 15 min, and most preferably from 1 min to 3 min.

After each of steps (a) to (g) the substrate may be purified. The kind of purification is not particularly limited, as long as the substrate and the dendrimer structures are not impaired. For example, the patterned substrate may be washed once or several times with one or various solvent(s), such as acetone and ethanol, and then be dried, for example, with compressed air or at the surrounding air. In particular, it is advantageous to purify the substrate between steps (e) and (f) and/or between steps (f) and (g).

A further aspect of the present invention particularly relates to the use of a patterned substrate according to the invention for the chemical synthesis of a chemical synthesis product, as a characterizing platform and/or as a platform for cell treatment/cell cultivation. The above definitions and embodiments apply to this aspect of the present invention in an analogous manner. The patterned substrate according to the invention is suitable for the combination of chemical synthesis, analytical characterization and cell treatment/cell cultivation or respectively only for one (or two in an arbitrary combination) of the three subsectors. In a preferred embodiment of the use according to the invention the patterned substrate is first used for the chemical synthesis of a chemical synthesis product and subsequently as a characterizing platform for characterizing the chemical synthesis product and/or for the treatment of at least one cell with the chemical synthesis product on the patterned substrate.

The chemical synthesis is not particularly limited. Thus, the skilled person may use the common methods. The application of the substances (as a pure substance or in solution) may be carried out, for example, by a dispenser, by discontinuous wetting, wherein a large drop of a solution is led over the surface, wherein smaller microdroplets are spontaneously formed on the first regions, or manual pipetting. Solvents may, for example, be removed under reduced pressure and added by the above-mentioned application means. Solvents and reagents may be added and removed also by sandwiching with a second patterned substrate. To this end, a solution is applied onto a second patterned substrate on the first regions and the second substrate and the first substrate are superimposed, such that the droplets on the first regions of the second substrate are contacted with the first regions of the first substrate.

The methods of characterization, which may be applied when using the patterned substrate according to the invention as a characterizing platform, are not particularly limited. Thus, common methods of analysis may be applied. In particular, it is advantageous to apply methods of analysis requiring an electrically conductive substrate, such as MALDI-TOF MS and scanning electron microscopy, since the patterned substrate according to the invention is able to provide the same without the necessity of a sample transfer. Solvents, reagents, etc., may be, for example, applied and removed as described above.

The cell treatment methods (preferably in vitro) are not particularly limited and are known by the skilled person. Examples for corresponding cell treatment methods are a toxicity screening, transformation methods, transfections methods and active agent screenings. For example, cells, cell suspensions, solvents, reagents, etc., may be applied and removed as described above. In principle, in vivo treatment methods are possible, too. For example, droplets with fish (embryos) (e.g., zebra danio or medaka) may be produced, the same may be treated with a chemical synthesis product and the effects may then be investigated.

In a cell treatment method, for example, droplet arrays with a cell suspension may be produced and the cells may then be cultivated on the patterned substrate according to the invention. The cells could then also be treated with active ingredients which have not been synthesized on the patterned substrate according to the invention. In addition, for example, a cell suspension to be treated may be applied on the single first regions of the patterned substrate according to the invention having chemical synthesis products produced thereon beforehand. Prior to that the solvent, wherein the chemical synthesis products are present, may be removed, for example, in order to avoid possible negative consequences on the cells. After that a cell suspension (in vitro and/or in vivo) may be applied on the patterned substrate according to the invention by the above-described methods. The cell suspension may be treated with additives known by the skilled person.

By a surface modification of substrates (for example, glass specimen slides, etc.) and their subsequent surface patterning the present invention preferably allows to produce a platform, the surface of which preferably is strongly hydrophilic and at the same time has omniphilic spots, which are delimited from each other by preferably strongly hydrophobic and at the same time omniphobic regions. This new surface functionalisation preferably allows the forming of droplet arrays with solutions having a low and high surface tension and is thus suitable to produce droplet arrays with organic solvents for chemical synthesis and droplet arrays with aqueous solvents for (cell) biological screenings.

The active working time for the manufacturing of, for example, poly(thioether) dendrimers of the generation 3 (G3), including a subsequent patterning, is only about 15 minutes. Thus, it is a fast method, which in addition can be easily parallelized and automated. The material costs of, for example, poly(thioether) dendrimer slides (in the following dendrimer slides in short) are significantly lower compared to the material costs of conventional HSTL slides.

Since the surface modification of the patterned substrate according to the invention is a covalent modification, the surface of the substrate has a high mechanical stability, for example, compared to HSTL slides. The application of an additional polymer layer (as it is necessary with HSTL slides) is not necessary anymore, whereby additional working steps may be saved, the manufacturing process is simplified, the working time is shortened, and thus the manufacturing costs are more and more minimized. Since the polymer layer is missing, for example, corresponding dendrimer slides are transparent at any time and may thus be investigated by visual analysis methods (such as (transmitted-light) microscopy). Furthermore, the patterned substrate according to the invention may preferably be purified and reused without loss of the surface patterning.

With the patterned substrate according to the invention, it does not have to be considered anymore which type of slide has to be used when planning the synthesis. With the corresponding dendrimer slides now a type of slide is available, which is preferably compatible with all solvents. Compared to the prior art, two different types of slides (LSTL and HSTL) are no longer necessary in order to combine the processes of the chemical synthesis with, for example, a biological screening. Dendrimeric slides now allow a combinatorial synthesis in a liquid phase in an array format in a miniaturized and parallelized form, however, also a solid phase synthesis is preferably supported, wherein the yield is preferably raised by an increased surface loading capacity compared to LSTL slides. Due to preferably missing physical boundaries between the spots—as it is the case, for example, with microtiter plates—the array may be extremely miniaturized. Since all droplets are preferably located on one plane without wells, the complete array may be further reacted in a single step, for example, by contacting it with a further array. In this case, in contrast to microtiter plate concepts, the single substances do not have to be pipeted out of the corresponding wells.

The patterned substrate according to the invention for the first time preferably allows a direct connection between chemical synthesis of a molecular library with the subsequent cell biological evaluation in the same array on only one single substrate, in particular slide. After the synthesis is completed, the (organic) solvent (having a low surface tension) may be evaporated and directly after that a droplet array having a cell suspension may be provided on the same substrate in the same array. A transfer of the synthetisized compounds onto another platform, which is cell compatible, is not necessary anymore, whereby working steps and materials are saved, which in turn lowers the costs for carrying out the experiments. Preferably, the new substrate surface has an excellent compatibility with cells (a very high cell viability).

Furthermore, the patterned substrate according to the invention preferably allows a patterning of conductive surfaces (e.g., indium-tin oxide-coated surfaces), while the conductivity is maintained, such that a droplet array with solutions having a low and high surface tension may be formed on the flat substrate. This property allows to additionally use the platform in analytical methods requiring an electrically conductive surface of the platform, such as MALDI-TOF MS and SEM. A transfer between the synthesis and characterization platform is preferably not necessary anymore.

The patterned substrate according to the invention preferably combines all regions of the early active ingredient development in the miniaturisized and parallelized array format. Preferably, all of combinatorial synthesis in a liquid (but also on a solid) phase, analytical characterization (for example, by MALDI-TOF MS, SEM or secondary ion mass spectrometry (ToF-SIMS)), and biological screening (for example, in cell experiments) are allowed on one single slide. A transfer of the substances between the single regions is not necessary anymore. Adding of additional reagents/cell suspension/etc., and the removal of single or all droplets is particularly simple by the preferably open and flat structure of the droplet arrays, for example, by contacting with a further array, manual pipeting or by dispenser systems.

The Figures show:

FIG. 1: Schematic illustration of the chemical structure of a poly(thioether) dendrimer of the third generation starting from a core (G0).

Figure 2:
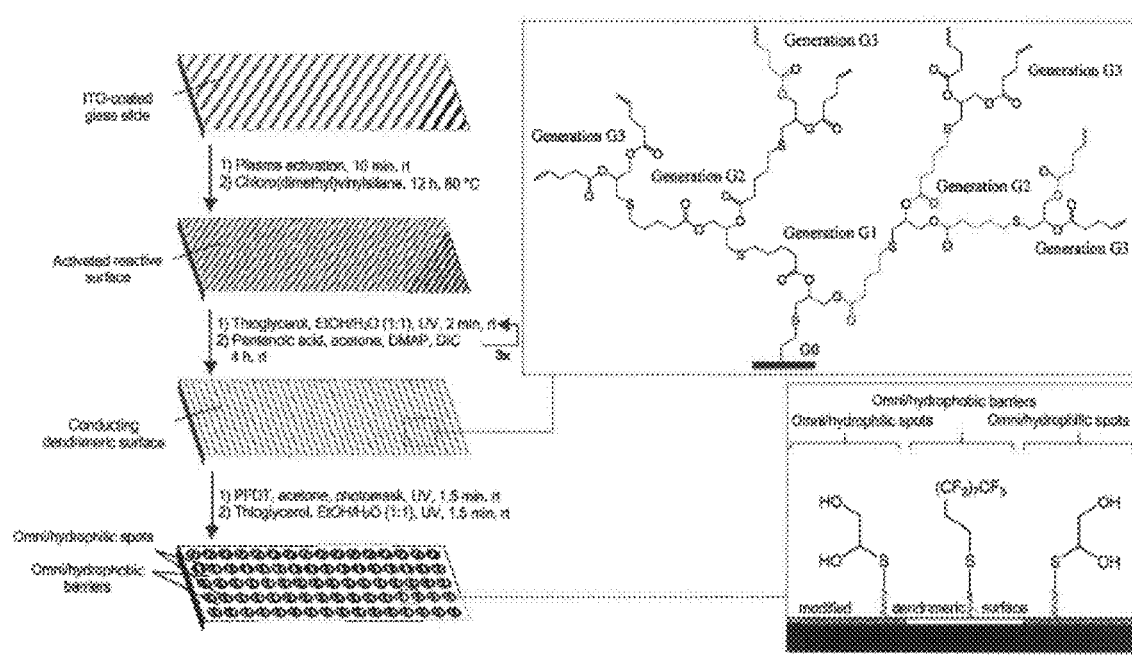

FIG. 2: Manufacturing process of patterned dendrimeric surfaces. First, a glass surface (or a glass-like surface, such as indium-tin oxide (ITO)) is activated and modified with chloro(dimethyl)vinylsilane. After that the dendrimeric structure is synthesized in a repeating photochemical thiolene-click reaction with thioglycerol, followed by an esterification with 4-pentenoic acid. The patterning of the surface is carried out with 1H,1H,2H,2H-perfluorodecanethiol (PFDT) and thioglycerol to produce hydrophilic/omniphilic spots, which are delimited from each other by hydrophobic/omniphobic barriers.

Figure 3:
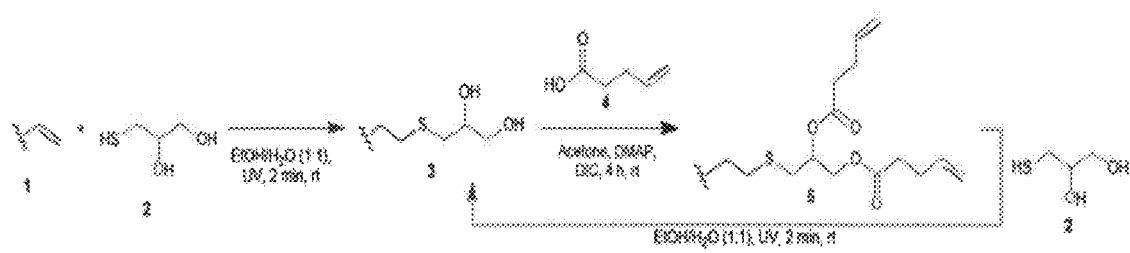

FIG. 3: Reaction cycle for synthesizing dendrimeric structures at a surface. The cycle consists of a photochemical thiol-ene-click reaction with thioglycerol (compound 2), followed by an esterification with 4-pentenoic acid (compound 4).

Figure 4:
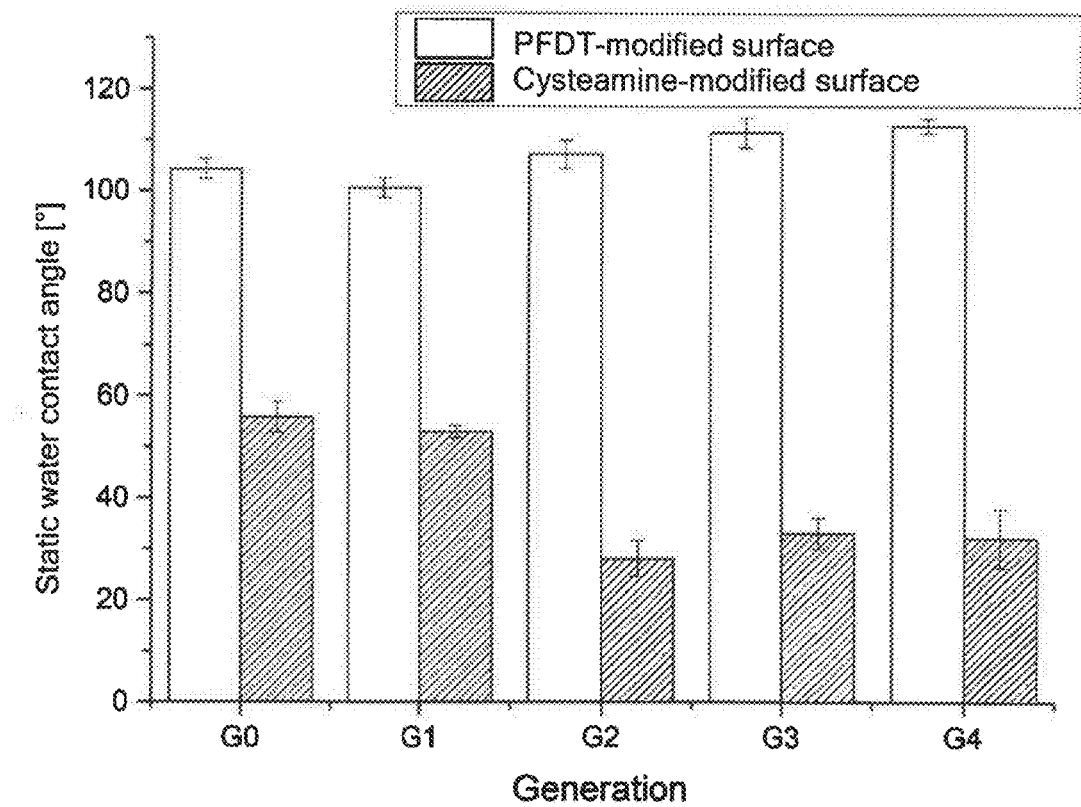

FIG. 4: Measurement of the static water contact angle on PFDT- and cysteamine-modified regions on dendrimer slides of generation G0 (corresponds to conventional LSTL slides) to generation G4.

Figure 5:
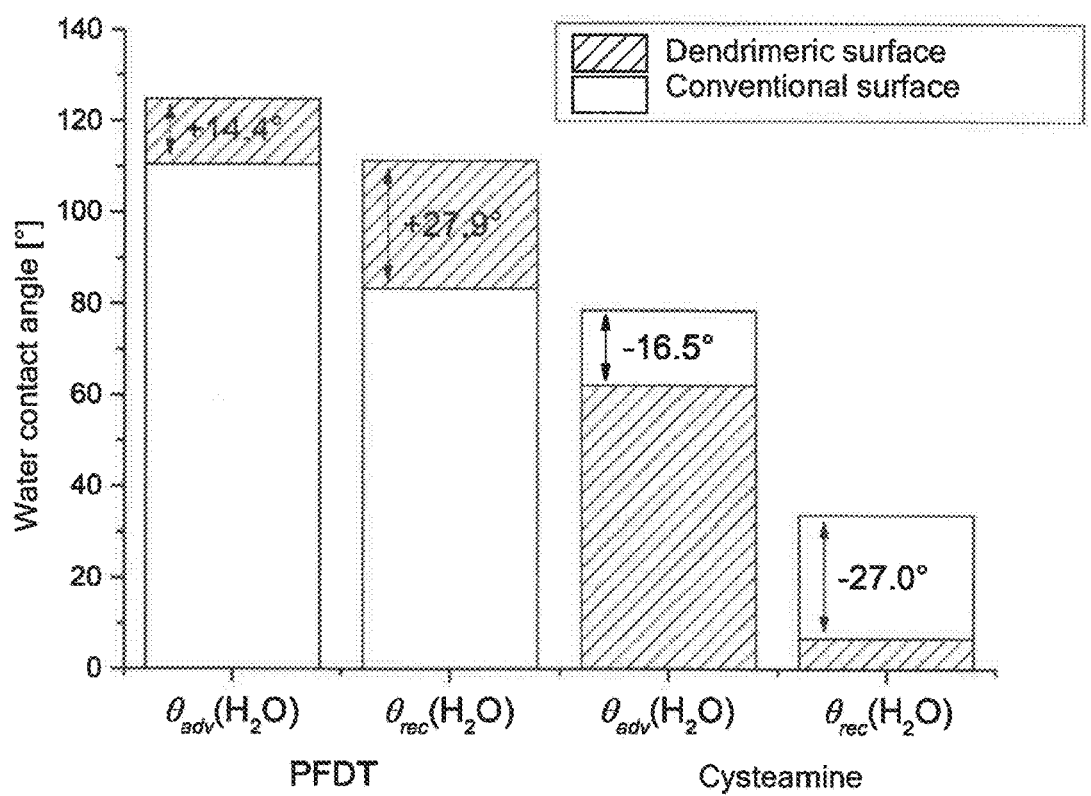

FIG. 5: Comparison of the advancing angle ($\theta_{adv}$) and the receding angle ($\theta_{rec}$) of water droplets on PFDT-modified and cysteamine-modified regions between conventional slides (LSTL slides and G0 slides, respectively) with dendrimer slides of generation G3.

Figure 6:
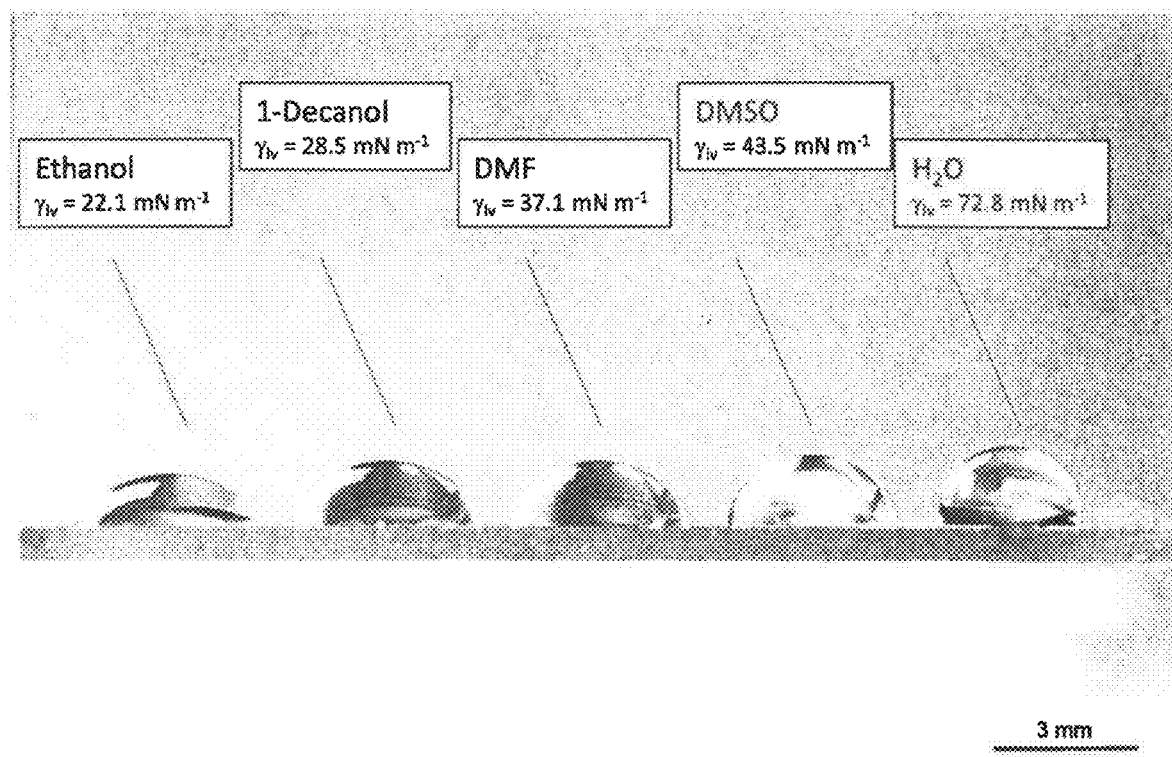

FIG. 6: Droplets of different solvents (low surface tension (ethanol) to high surface tension (water) from left to right) on a patterned dendrimer slide.

Figure 7:
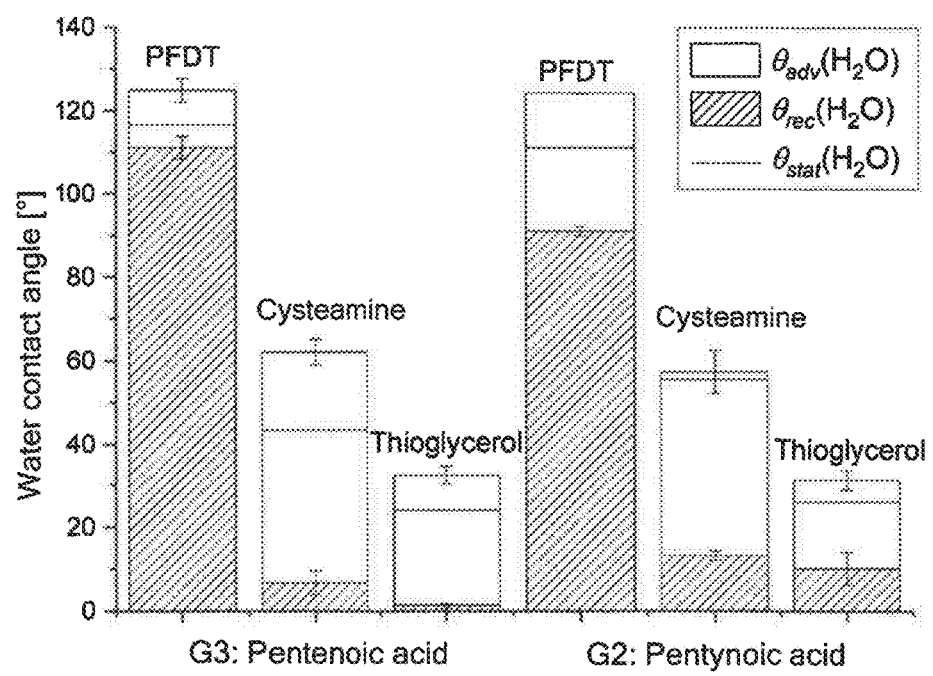

FIG. 7: Comparison of the water contact angle of differently modified dendrimer slides, which were manufactured by various methods (thiol-ene and thiol-yne chemistry).

Figure 8:
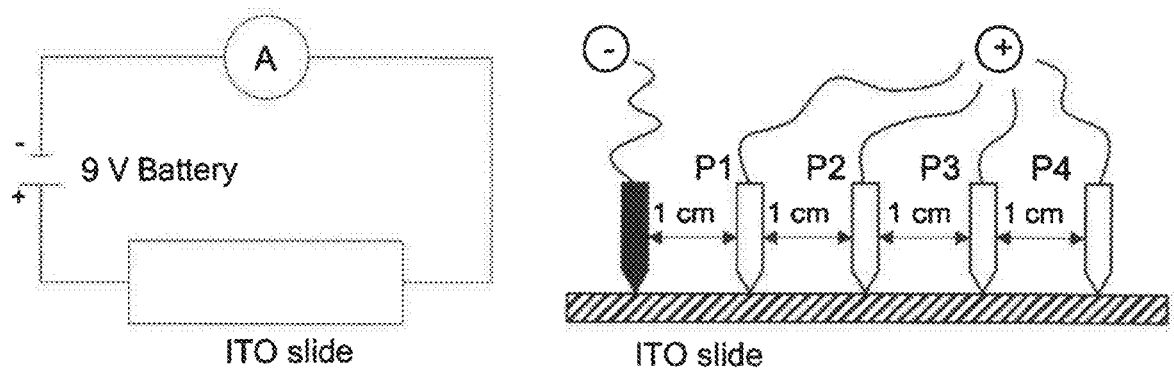

FIG. 8: Measurement of the electrical current at four different points (each at a distance of 1 cm) on the surface of dendrimer slides.

FIG. 9a-d: Results of the cell viability screening. (a) On spots of the dendrimer slides, all three tested cell lines (HeLa, HEK293T, and Jurkat) have shown an excellent cell viability of more than 90%. (b) Microscopy image of HeLa cells (viability: 92.5±3.3%) on spots of dendrimer slides. (c) Microscopy image of HEK293T cells (viability: 98.2±0.2%) on spots of dendrimer slides. (d) Microscopy image of Jurkat cells (viability: 99.2±0.1%) on spots of dendrimer slides. Scale indicator: 50 μm.

Figure 10:
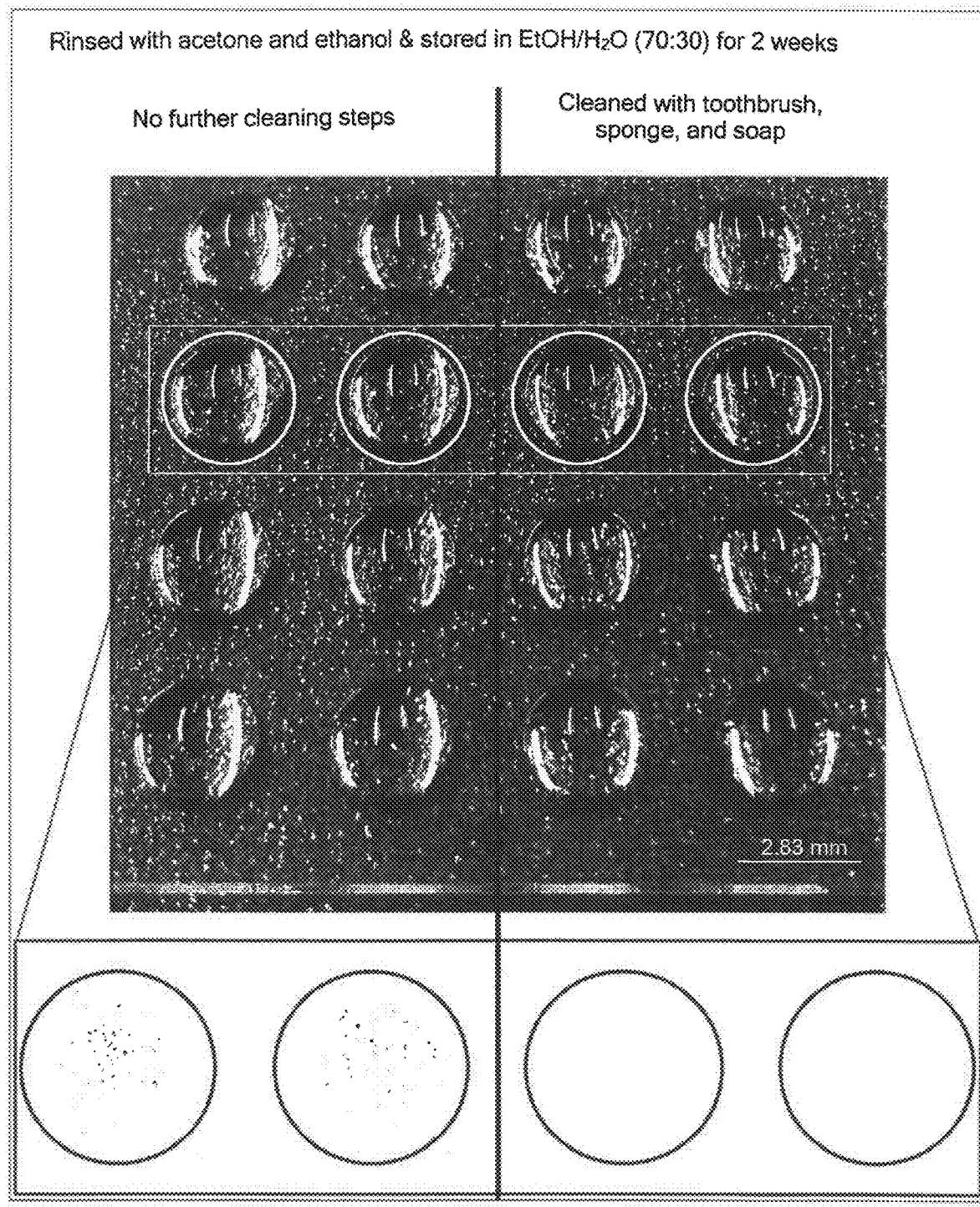

FIG. 10: Droplet array and fluorescence microscopic image in the propidiumiodide channel of purified dendrimer slides after cell experiments. For an easier visualisation a negative image has been produced from the fluorescence microscopic image in a subsequent image processing. After mechanical cleaning by a toothbrush, a sponge and soap no cell debris could be found on the surface. Droplet arrays may still be produced afterwards.

Figure 11:
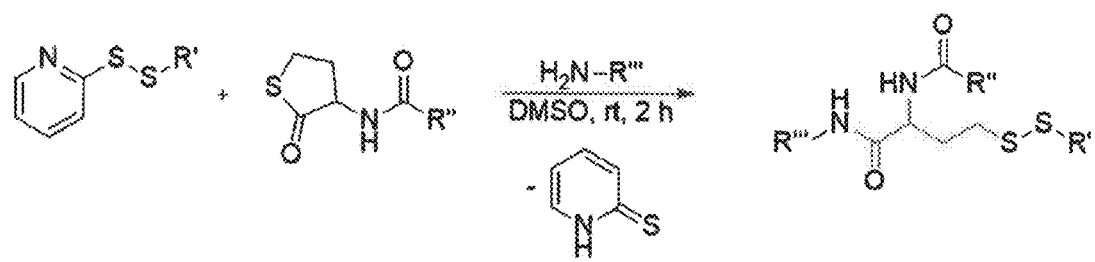
Figure 11:
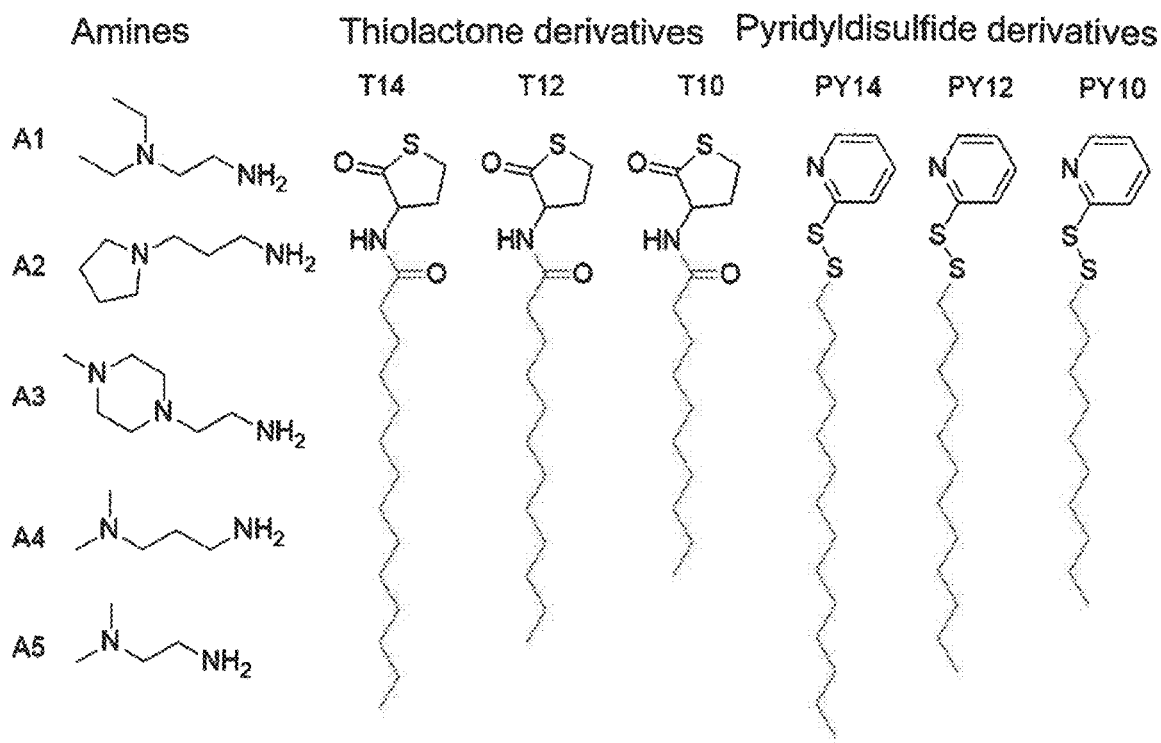

FIG. 11: 3 component reaction for synthesis of lipid-like molecules (lipidoids) and the precursor molecules used for the same. For synthesis, in each case 1.5 μL amine component and 1.5 μL thiolactone-pyridyldisulfide solution were combined on the spots of the array (round, diameter of 2.83 mm) by a dispenser.

Figure 12:
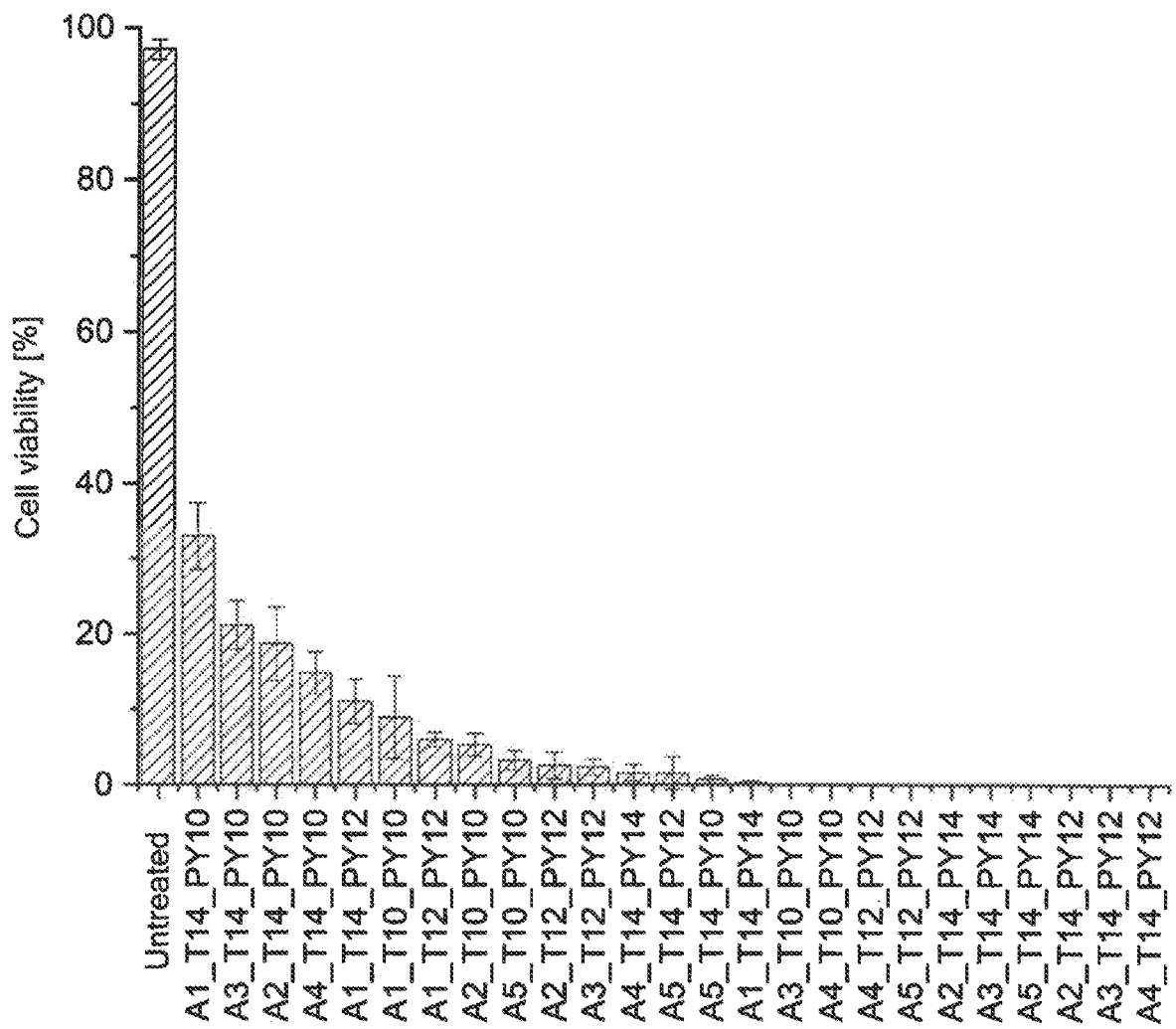

FIG. 12: Evaluation of the toxicity screening. The cell viability in [%] after 24 h of incubation of HEK293T cells, which have been seeded on a lipidoid library synthesized beforehand, is shown.

The present invention is discussed in more detail by the following non-limiting examples.

General

General Standard Operation Procedures:
Activation and Silanization of Slides (Holders):

In order to activate glass holders (for example, regular silicon oxide glass holders (Schott Glas) and indium-tin oxide-coated glass holders (ITO slides, Bruker)) the same were cleaned by plasma treatment for 10 minutes at room temperature. The silanization of the surface of the glass holder was carried out in a gas phase including 100 μL chloro(dimethyl)vinylsilane (Sigma-Aldrich) for 10 hours at 80° C. under vacuum (50 mbar). First, the surface was rinsed with acetone and then with ethanol and dried with compressed air.

General Standard Operation Procedure of a Cycle to Generate a Branch of the Dendrimer Structure (One Generation) Formed at a Smooth Surface with 4-Pentenoic Acid:

On the surface of the slides, which were silanized beforehand, 250 μL of a 10 vol % 1-thioglycerol solution (in ethanol/$H_2O$ (1:1), 10 mg·$mL^{-1}$ 2,2-dimethoxy-2-phenylacetophenone (DMPAP, Sigma-Aldrich); Sigma-Aldrich) were applied. After that the solution was covered with a quartz glass and the slide was exposed with UV light having a wavelength of 260 nm (OAI model 30) at an intensity of 3 mW·$cm^{-2}$ for 2 minutes at room temperature. The surface was rinsed with ethanol and dried with compressed air. The slide was immersed in an esterifying solution (45 mL acetone (Merck), 56 mg 4-(dimethylamino)pyridine (DMAP, Novabiochem), 125 μL 4-pentenoic acid (Sigma-Aldrich) and 180 μL N,N'-diisopropylcarbodiimide (DIC, Alfa Aesar)) cooled to −20° C. for 4 hours with stirring and then the temperature of the reaction solution was slowly raised to room temperature. First, the surface was washed with acetone and then with ethanol and dried with compressed air.

General Standard Operation Procedure of a Cycle to Generate a Branch of the Dendrimer Structure (One Generation) Formed at a Smooth Surface with 4-Pentynoic Acid:

On the surface of the slides, which were silanized beforehand, 250 μL of a 10 vol % 1-thioglycerol solution (in ethanol/$H_2O$ (1:1), 10 mg·$mL^{-1}$ 2,2-dimethoxy-2-phenylacetophenone (DMPAP, Sigma-Aldrich); Sigma-Aldrich) were applied. After that the solution was covered with a quartz glass and the slide was exposed with UV light having a wavelength of 260 nm (OAI model 30) at an intensity of 3 mW·$cm^{-2}$ for 2 minutes at room temperature. The surface was rinsed with ethanol and dried with compressed air. The slide was immersed in an esterifying solution (45 mL acetone (Merck), 56 mg 4-(dimethylamino)pyridine (DMAP, Novabiochem), 111.6 mg 4-pentynoic acid (Sigma-Aldrich) and 180 μL N,N'-diisopropylcarbodiimide (DIC, Alfa Aesar)) cooled to −20° C. for 4 hours with stirring and then the temperature of the reaction solution was slowly raised to room temperature. First, the surface was washed with acetone and then with ethanol and dried with compressed air.

Patterning of the Surface with Perfluorodecanethiol and 1-Thioglycerol:

300 μL of a 20 vol % 1H,1H,2H,2H-perfluorodecanethiol solution (10 mg·$mL^{-1}$ 2,2-dimethoxy-2-phenylacetophenone (DMPAP, Sigma-Aldrich); Sigma-Aldrich) in acetone (Merck) were applied on a surface, which was modified beforehand, and exposed through a photomask (Rose Fotomasken) for 1.5 minutes at room temperature with UV light having a wavelength of 260 nm (OAI model 30) at an intensity of 3 mW·$cm^{-2}$. The surface was rinsed with acetone and dried with compressed air. 300 μL of a 10 vol % 1-thioglycerol solution (in ethanol/$H_2O$ (1:1), 10 mg·$mL^{-1}$ 2,2-dimethoxy-2-phenylacetophenone (DMPAP, Sigma-Aldrich); Sigma Aldrich) were applied on the surface and exposed through a quartz glass with UV light having a wavelength of 260 nm (OAI model 30) at an intensity of 3 mW·$cm^{-2}$ for 1.5 minutes at room temperature. The surface was rinsed with ethanol and dried with compressed air.

Patterning of the Surface with Perfluorodecanethiol and Cysteamine Hydrochloride:

300 µL of a 20 vol % 1H,1H,2H,2H-perfluorodecanethiol solution (10 mg·mL$^{-1}$ 2,2-dimethoxy-2-phenylacetophenone (DMPAP, Sigma-Aldrich); Sigma-Aldrich) in acetone (Merck) were applied on a surface, which was modified beforehand, and exposed through a photomask (Rose Fotomasken) for 1.5 minutes at room temperature with UV light having a wavelength of 260 nm (OAI model 30) at an intensity of 3 mW·cm$^{-2}$. The surface was rinsed with acetone and dried with compressed air. 300 µL of a 10 wt % cysteamine hydrochloride solution (in ethanol/H$_2$O (1:1), 10 mg·mL$^{-1}$ 2,2-dimethoxy-2-phenylacetophenone (DMPAP, Sigma-Aldrich); Alfa Aesar) were applied on the surface and exposed through a quartz glass with UV light having a wavelength of 260 nm (OAI model 30) at an intensity of 3 mW·cm$^{-2}$ for 1.5 minutes at room temperature. The surface was rinsed with ethanol and dried with compressed air.

Water Contact Angle Measurements:

The surfaces of the glass holders were characterized by water contact angle measurements using the Drop Shape Analyzer DSA25 (Krüss). The advancing angle ($\theta_{ac}$), the receding angle ($\theta_{rec}$) and the static angle ($\theta_{stat}$) were measured. To this end, 40 µL deionized water were applied on the respective surface at a rate of 0.3 µL·s$^{-1}$ and withdrawn by suction again and in the course thereof the corresponding angles were measured.

Example 1: Preparation of Dendrimer Slides with 2-Pentenoic Acid

The preparation of a dendrimer slide is schematically shown in FIG. 2.

Regular silicon oxide glass holders (Schott Glas) and indium-tin oxide-coated glass holders (ITO slides, Bruker) were used for the preparation of dendrimer slides. For activation, the glass holders were cleaned by a plasma treatment and silanized, as indicated in the general standard operation procedure. The surfaces of the holders were silanized in order to render them more reactive by introducing double bonds (see structure 1 in FIG. 3).

After that the surfaces were further functionalized in order to form dendrimeric structures thereon. FIG. 3 shows the two iteratively running synthesis steps which constitute one cycle and one degree of branching and thus one generation of the surface structure. After reacting the reactive surfaces, which have been functionalized with double bonds (see structure 1 in FIG. 3) with thioglycerol (see compound 2 in FIG. 3) in a first step of the cycle, the surfaces have numerous hydroxy groups (see structure 3 in FIG. 3), which are reacted in the second step of the cycle in an esterification with 4-pentenoic acid (see compound 4 in FIG. 3). Thus, the hydroxy terminal groups of the surfaces are converted into terminal groups having double bonds (see structure 5 in FIG. 3). These double bonds may again be reacted in a further cycle in a thiol-ene-reaction with thioglycerol (see compound 2 in FIG. 3; right side), whereby again functional hydroxy terminal groups are produced, and after that may be reacted with 4-pentenoic acid. The two steps of the cycle may be further repeated, wherein in each passing of the cycle the degree of branching raises by $2^n$ (n: number of cycles). The produced dendrimers may be chemically denoted as poly(thioether) dendrimers.

The above-described processes were applied on the holders by carrying out the general standard operation procedure with regard to one cycle (one generation) for generating a branch of the dendrimer structure formed at a smooth surface with 4-pentenoic acid. In total, the cycle was carried out three times, as shown, for example, in FIG. 2. After the third passing of the cycle the number of originally one immobilized double bond could be raised to eight double bonds (see FIG. 1).

After that those terminal double bonds were site-specifically reacted in further photochemical thiol-ene-click reactions with strongly hydrophobic (1H,1H,2H,2H-perfluorodecanethiol (PFDT)) and hydrophilic (thioglycerol) molecules by a photomask or by a laser beam. Thus, the surfaces could be patterned such that thioglycerol-functionalized spots were obtained, which are separated from each other by boundaries of PFDT-funktionalized barriers.

The above-described terminal functionalizations were applied on the holders by carrying out the general standard operation procedure concerning the patterning of the surface with periluorodecanethiol and 1-thioglycerol.

In this case, spots having different diameters, e.g. between 500 µm and 2.83 mm, and an arbitrary geometrie could be produced.

Example 2: Preparation of Dendrimer Slides with 2-Pentynoic Acid

In analogy to example 1, a dendrimeric surface modification was also carried out with 4-pentynoic acid instead of 4-pentenoic acid. In this case, the dendrimeric structure is formed by a thiol-yne-reaction and finally patterned. The repeating units were applied on the holder using the general standard operation procedure with respect to one cycle (one generation) to generate a branch of the dendrimer structure formed on a smooth surface with 4-pentynoic acid.

Example 3: Investigation of the Influence of the Degree of Branching of Different Dendrimer Generations on the Static Water Contact Angle The influence of the degree of branching of different dendrimer generations on the static water contact angle was investigated. To this end, dendrimer slides were prepared, which were esterified with 4-pentenoic acid. In the last step, respective modifications of the surfaces were carried out with PFDT in order to characterize the properties of the hydrophobic/omniphobic boundaries (i.e., the second regions), and with cysteamine in order to characterize the properties of the hydrophilic/omniphilic spots (i.e., the first regions). The results are shown in FIG. 4.

Already after the second generation of the dendrimer slides a raise of the static contact angles on the PFDT-modified regions and a clear decline of the static contact angle on the cysteamine-modified regions can be noted. After that the contact angle changes only slightly. Substrates having a third dendrimer generation had, for example, static contact angles on the PFDT-modified regions of $\theta_{stat}(H_2O)=111.5\pm2.9°$ and on the cysteamine-modified regions of $\theta_{stat}(H_2O)=33.0\pm3.0°$.

Example 4: Comparison of the Advancing Angle ($\theta_{ad}v$) and the Receding Angle ($\theta_{rec}$) of Water Droplets on PFDT-Modified and Cysteamine-Modified Regions Between Conventional Slides (LSTL Slides and G0 Slides, Respectively) with Dendrimer Slides of the Generation G3

Advancing angles ($\theta_{adv}$) and receding angles ($\theta_{rec}$) of water droplets on PFDT-modified and cysteamine-modified regions of conventional slides (LSTL slides and G0 slides, respectively) and dendrimer slides of the generation G3 were measured. The results are shown in FIG. 5. Both angles were clearly increased by the dendrimeric surface on PDFT-modified regions and clearly decreased on cysteamine-modified regions. Due to the large difference between the receding angle on PFDT-modified regions and cysteamine-modified regions, droplet arrays on dendrimer slides may be generated both with solvents with low as well as with high surface tension. However, on conventional LSTL slides without dendrimeric surface no droplet arrays can be formed. The difference between the receding angle on PFDT-modified regions ($\theta_{rec}(H_2O)$=83.3°) and the receding angle on cysteamine-modified regions ($\theta_{rec}(H_2O)$=33.7°) is clearly smaller in conventional LSTL slides than in dendrimer slides according to the invention (see FIG. 5).

The third dendrimer-generation shows a clearly larger difference of the receding contact angle (PFDT: $\theta_{rec}(H_2O)$ =111.2°; cysteamine: $\theta_{rec}(H_2O)$=6,7°). Due to the large difference of the receding angle on the two differently modified regions also droplet arrays with aqueous solvents having a high surface tension may be generated on patterned dendrimeric surfaces. Since the modification of the surface is a direct covalent modification, also solvents having a low surface tension may be applied without diffusion out of the spots and cross-contamination resulting therefrom (see FIG. 6).

Example 5: Comparison of the Water Contact Angle of Differently Modified Dendrimer Slides, which were Prepared by Different Methods (Thiol-Ene and Thiol-Yne Chemistry)

Dendrimeric structures were generated by photochemical thiol-ene-click reactions using 4-pentenoic acid and by photochemical thiol-yne-click reactions using 4-pentynoic acid on different flat substrates. Since the degree of branching in a thiol-yne reaction is once more doubled compared with a thiol-ene reaction, the water contact angles of the second generation of thiol-yne generated dendrimeric surfaces were compared with the third generation of thiol-ene generated dendrimeric surfaces (see FIG. 7).

While the advancing angles of the dendrimer surfaces on PFDT-functionalized regions prepared with 4-pentynoic acid ($\theta_{adv}(H_2O)$=124.2±0.1°) and cysteamine-functionalized regions ($\theta_{adv}(H_2O)$=57,3±5.2°) are almost identical with dendrimer surfaces prepared with 4-pentenoic acid, the receding angle of the dendrimer surfaces on the PFDT-functionalized regions prepared with 4-pentynoic acid ($\theta_{rec}(H_2O)$=91.0±1.1°) is slightly lower and on the cysteamine-functionalized regions ($\theta_{rec}(H_2O)$=13.2±1.1°) is slightly higher than on the corresponding regions with 4-pentenoic acid dendrimers.

Besides the investigations of different acid components for the synthesis of the dendrimer, different reagents for the final surface patterning were investigated, too (see FIG. 7). A functionalization with thioglycerol results in a further clear improvement of the hydrophilic/omniphilic properties of the surface. Dendrimeric surfaces (4-pentenoic acid) functionalized with thioglycerol of the third generation have an advancing angle of $\theta_{adv}(H_2O)$=32.6±2.2° and a receding angle of $\theta_{rec}(H_2O)$=1.2±0.6°, corresponding to a halving of the corresponding angles compared to the functionalisation with cysteamine (see FIG. 7).

Example 6: Modification of Conductive Surfaces with Dendrimer Structures

ITO-coated glass slides were modified with dendrimer structures according to the invention. On the corresponding substrates, droplet arrays having small and large surface tension could be generated, too.

The electric current was measured at respective four positions (at a respective distance of 1 cm) on the surface of the modified glass slides in order to check the provision of the conductivity (see FIG. 8). A 9 V battery having a residual current of 1.1 A and a residual voltage of 8.5 V was used for the measurement.

In this manner, after each step of preparing the dendrimeric surface the electric current was measured (see Table 1). Furthermore, the influence of the solvent in the esterification steps was investigated.

TABLE 1

Measurement of the electrical current at four positions (P1-4; see FIG. 8) on surfaces after various steps in the production of dendrimeric slides.

| Step | P1 [A] | P2 [A] | P3 [A] | P4 [A] | Solvent | Time after start [d] |
|---|---|---|---|---|---|---|
| Non-treated (positive control) | 0.048 | 0.034 | 0.032 | 0.024 | | 0 |
| Plasma activation | 0.042 | 0.035 | 0.031 | 0.023 | | 0 |
| Silanization | 0.025 | 0.021 | 0.020 | 0.015 | | 1 |
| 1. Esterification | 0.024 | 0.021 | 0.015 | 0.011 | Acetone | 1.5 |
| 1. Esterification | 0.024 | 0.021 | 0.020 | 0.014 | DCM | 1.5 |
| 2. Esterification | 0.026 | 0.022 | 0.019 | 0.017 | Acetone | 2 |
| 2. Esterification | 0.025 | 0.022 | 0.019 | 0.017 | DCM | 2 |
| 3. Esterification | 0.028 | 0.026 | 0.025 | 0.021 | Acetone | 2.5 |
| 3. Esterification | 0.028 | 0.021 | 0.020 | 0.020 | DCM | 2.5 |
| Patterned | 0.032 | 0.028 | 0.025 | 0.022 | Acetone | 2.5 |
| Patterned | 0.027 | 0.024 | 0.021 | 0.018 | DCM | 2.5 |
| Regular glass slide (negative control) | 0 | 0 | 0 | 0 | Acetone | 0 |
| Patterned glass slide (G3; negative control) | 0 | 0 | 0 | 0 | Acetone | 2.5 |

No difference between the use of acetone and dichloromethane (DCM) could be noted. The electric current halves after the silanization, then, however, remains constant up to the final patterning (see Table 1). Thus, no conductive platforms could be obtained. Thus, after the completed on-chip synthesis of a substance, also a direct on-chip characterization by MALDI-TOF MS or other analysis methods requiring an electrically conductive platform may be carried out.

Example 7: Cell Viability Screening on Dendrimer Slides

Cell viability screenings with various cell lines (adherend cells: HeLa, HEK293T; suspension cells: Jurkat) were carried out in order to evaluate the compatibility of the surface of the patterned substrates according to the invention with (cell) biological experiments.

To this end, HeLa and HEK293T cells were cultivated in Dulbecco's Modified Eagle Medium (DMEM, Life Technologies) having 15% v/v fetal bovine serum (FBS; PAA Laboratories) and 1% v/v penicillin-streptomycin (Life Technologies). Jurkat cells were cultivated in RPMI 1640 Medium (Gibco) having 15% v/v FBS (PAA Laboratories) and 1% v/v penicillin-streptomycin (Life Technologies).

3 μL of a HeLa and HEK293T cell suspension each having a concentration of 50,000 cells/mL and 3 μL of a Jurkat-cell suspension having a concentration of 80,000 cells/mL were applied by a dispenser (I-DOT, Dispendix) per spot of the substrate. The diameter of the round spots was 2.83 mm and the distance between the spots was 1.67 mm. After 24 h of cultivation (at 37° C. and 5% $CO_2$ concentration) the cells were stained with Hoechst 33342 (1:900; 10 mg·mL$^{-1}$; Invitrogen) to determine the total cell number (staining of the cell nucleus) and propidiumiodide (PI; 1:1350; 1.00 mg mL$^{-1}$; Invitrogen) to determine the number of dead cells (staining of dead cells). The evaluation was carried out by fluorescence microscopy by a Keyence BZ9000 (Keyence) and the software ImageJ (Funktion: Analyze Particles). The number of viable cells was calculated from the difference of the total cell number and the number of dead cells. The cell viability was indicated as a quotient of the number of viable cells and the total number of cells in percent [%] (see FIG. 9).

Figure 9A:
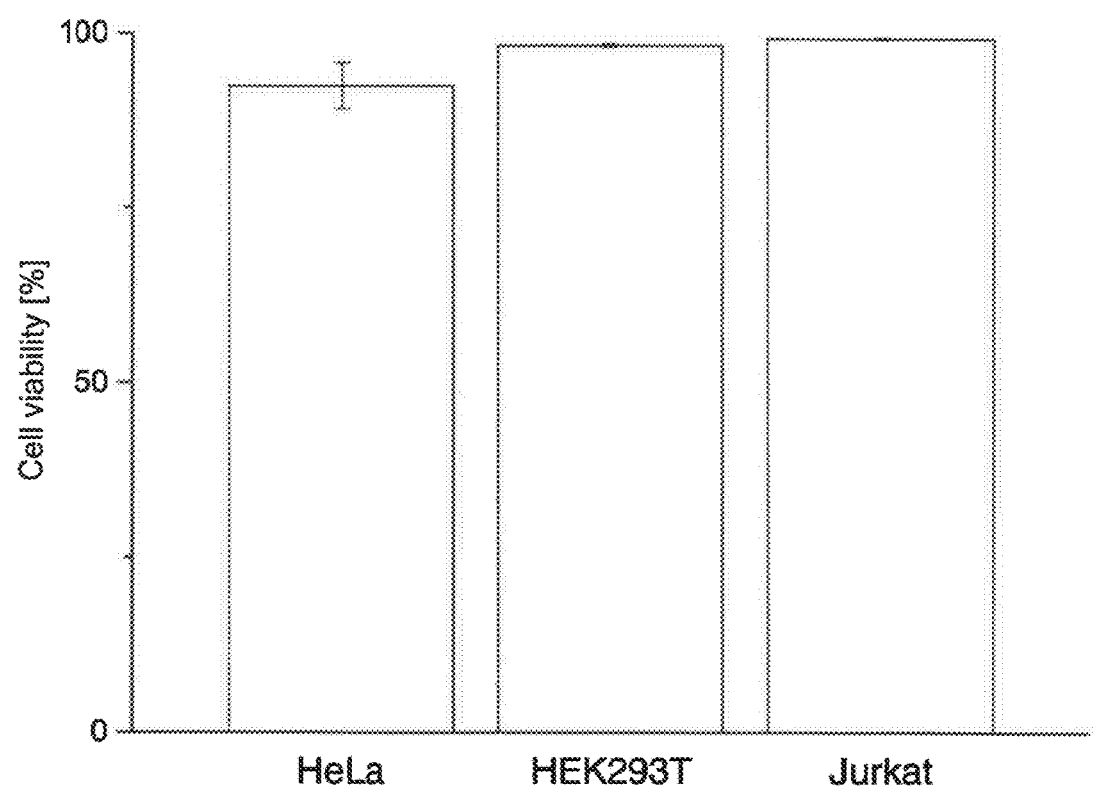
Figure 9B:
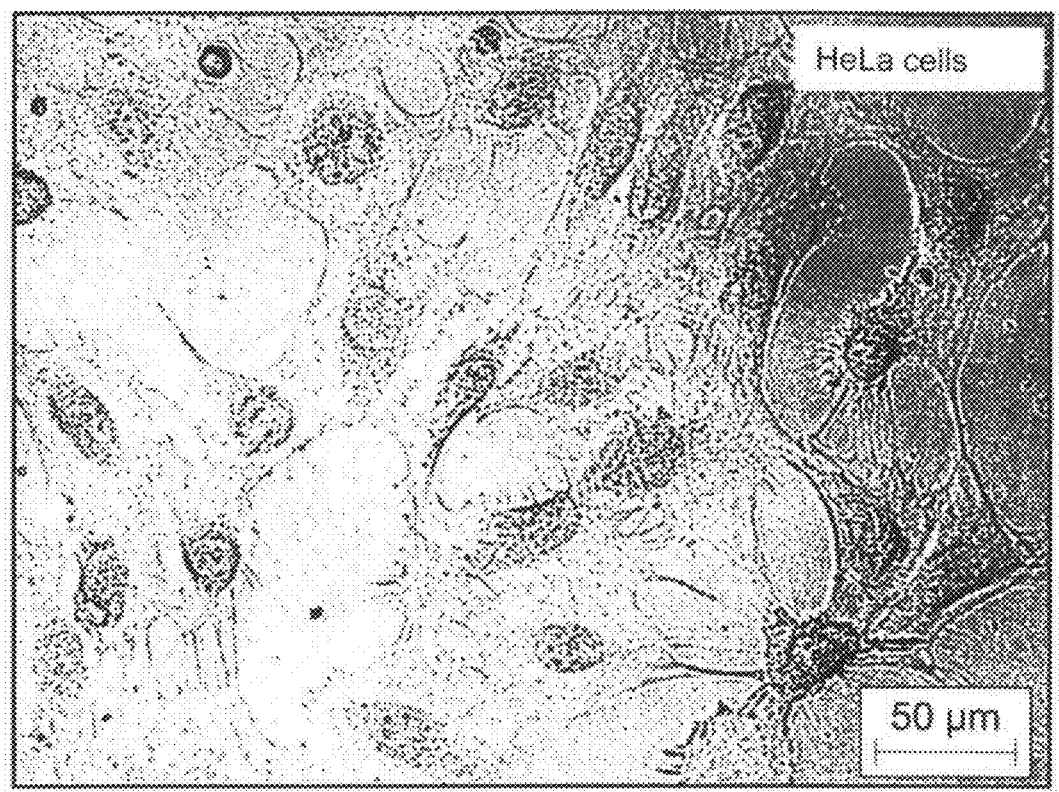
Figure 9C:
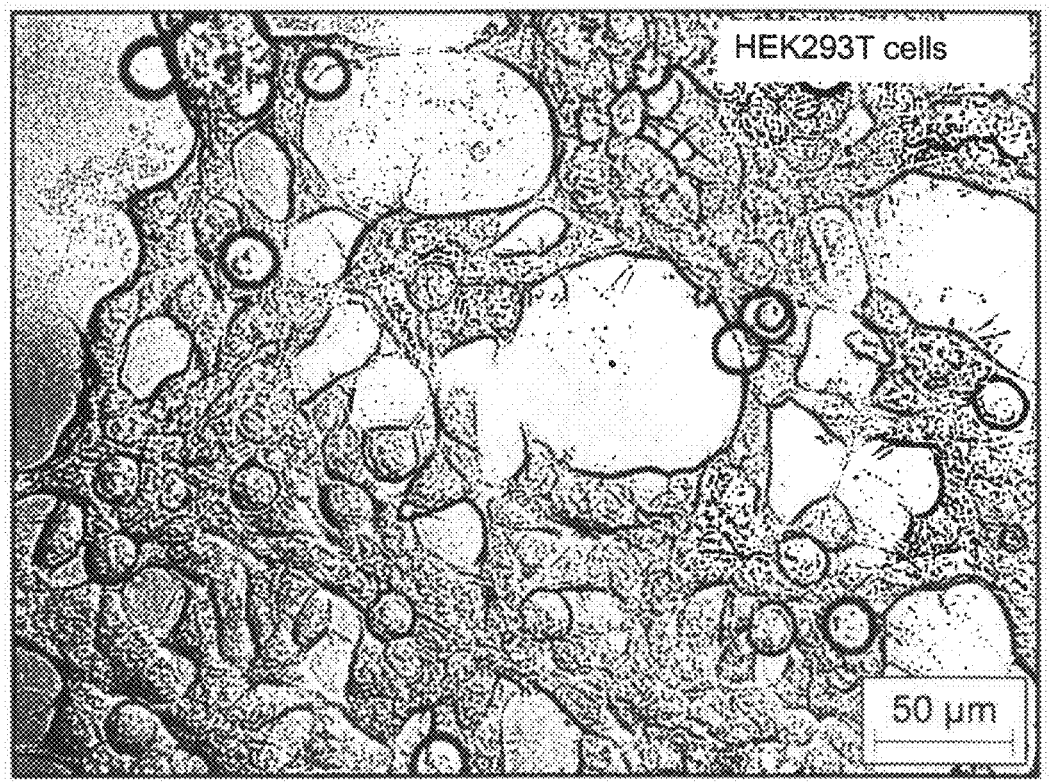
Figure 9D:
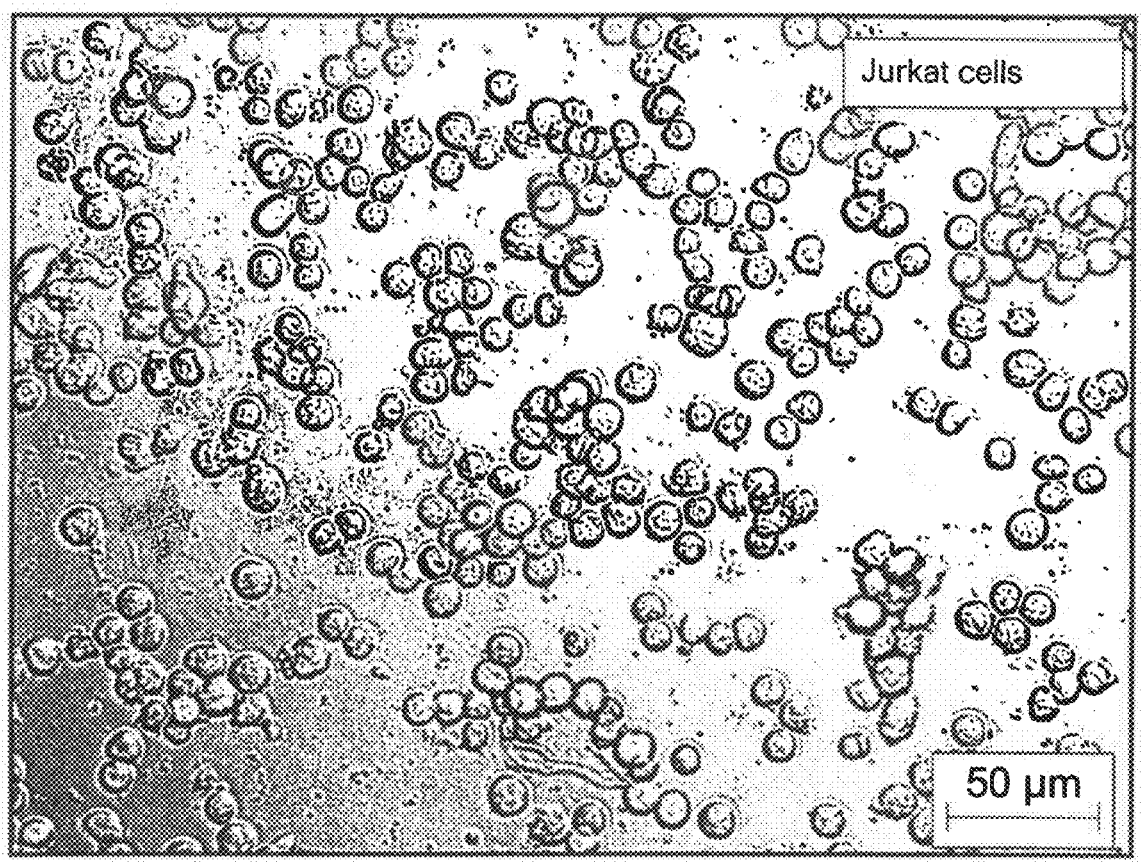

Any one of the tested cell lines demonstrated a very good cell viability (>90%) on the spots of the dendrimer slides (see FIG. 9a). Furthermore, all three tested cell lines have shown the respective typical morphology (see FIG. 9b-d). Thus, the patterned substrates according to the invention are excellently suitable for biological cell screenings.

Example 8: Reusability of the Dendrimer Slides

The dendrimer slides from example 7, which have been used for the biological cell viability screenings, were cleaned and tested as to whether they may be reused. To this end, the slides were first rinsed with acetone and ethanol, which resulted in a lysis of the cells remaining thereon. In this context, a cloudy staining of the spots indicated a precipitation of the proteins present in the cells. For sterilisation the slides were immersed in an aqueous 70 vol % ethanol solution for two weeks. After that the cloudiness of the spots was still visible.

Microscopic images have shown still existing cell debris on the surface of the spots. The staining of the dead cells by propidiumiodide was still visible by fluorescence microscopy, too. After that parts of the slide surface were mechanically cleaned by means of a commercially available toothbrush and soap and after that with a sponge. The slide was again rinsed with ethanol and acetone and dried with compressed air. FIG. 10 shows the result of the cleaning process.

A clear line between the mechanically cleaned surface and the non-cleaned surface can be observed in the propidiumiodide channel by fluorescence microscopy (see FIG. 10). Also by transmitted-light microscopy in visible light no cell debris on the mechanically cleaned spots of the dendrimer surface could be observed anymore. Nevertheless, droplet arrays could also be generated on the mechanically cleaned spots. No difference between the shape and volume could be observed between cleaned and non-cleaned spots (see FIG. 10). Thus, the surfaces of the used dendrimer slides are mechanically stable and reusable. In contrast, the surface of HSTL slides known from the prior art would be destroyed by this process.

Example 9: Toxicity Screening with Dendrimer Slides

The possibility of a chemical synthesis with a biological screening on a single patterned substrate according to the invention was investigated. To this end, first a library of 25 different lipid-like molecules (lipidoids) was synthesized in a combinatorial manner in a liquid phase on a dendrimer slide (round spots, diameter of 2.83 mm, barrier diameter of 1.67 mm). The synthesis is based on a three components reaction, wherein a primary amine (A1-A5) initiates the reaction by ring opening of a thiolactone (T10/T12/T14), and which terminates by a disulfide exchange with a pyridyldisulfide (PY10/PY12/PY14). The precursor molecules which were used are shown in FIG. 11.

For the combinatorial synthesis of the lipidoid library in each case 1.5 µL of the amine component (dissolved in DMSO; 1:24 v/v) (A1-A5) and 1.5 µL of a mixture (dissolved in DMSO) of thiolactone derivative (1.67 mg·mL$^{-1}$) and pyridyldisulfide derivative (1.75 mg·mL$^{-1}$) (mixtures: T10_PY10/T12_PY12/T14_PY14/T14_PY12/T14_PY10) were combined. The solutions were applied by dispensers (I-DOT, Dispendix) in a combinatorial format. After 2 hours reaction time at room temperature the solvent was removed under reduced pressure. After that 3 µL of a HEK293T cell suspension (50,000 cells/mL) were printed by a dispenser onto each spot of the array in order to determine the toxicity of the synthesis products. The slide was incubated for 24 hours at 37° C. and 5% $CO_2$ concentration and after that the cells were stained with Hoechst 33342 (1:900; 10 mg·mL$^{-1}$; Invitrogen) to determine the total cell number (staining of the cell nucleus) and propidiumiodide (PI; 1:1350; 1.00 mg·mL$^{-1}$; Invitrogen) to determine the number of dead cells (staining of dead cells). The evaluation was carried out by fluorescence microscopy (Keyence BZ9000 (Keyence)) and the software ImageJ (function: Analyze Particles). The number of viable cells was calculated from the difference of the total cell number and the number of dead cells. The cell viability was indicated as the quotient of the number of viable cells and the total number of cells in percent [%] (see FIG. 12).

As it can be seen in FIG. 12, all substances were found to be very toxic in the tested concentration. Having a cell viability of 33.0±4.4%, the lipidoid A1_T14_PY10 was found to be the least toxic. For the negative control with non-treated cells again an excellent cell viability of 97.2±1.3% could be observed. This clearly shows that the toxic effect was not caused by the surface and confirms the preceding cell viability screenings of example 7. In the following, the finding from this primary screening may serve to provide a lead structure for chemical structure-optimizing experiments.

Thus, it could be successfully shown that on patterned substrates according to the invention chemical synthesis in an aqueous phase may be directly combined with biological screenings on a single platform in a droplet array format.

The invention claimed is:

1. A patterned substrate comprising first regions and second regions on a surface of the substrate, wherein
   the first regions have first dendrimer structures and the second regions have second dendrimer structures;
   the dendrimer structures are each covalently connected with the substrate surface;
   the second regions enclose the first regions; and
   the second dendrimer structures have at least one structural element different from the structural elements of the first dendrimer structures;
   wherein the first dendrimer structures have terminal groups having the following general formula (4) or (5)

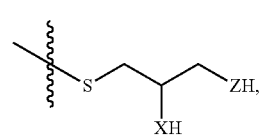

Formula (4)

wherein X and Z are independently from each other $NR^3$ or O, wherein each $R^3$ is independently from each other selected from the group consisting of hydrogen, an alkyl group, a cycloalkyl group, an aryl group, and a heteroaryl group;

Formula (5)

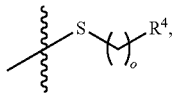

wherein $R^4$ is selected from the group consisting of $-NG^1G^2$, $-NO_2$, $-CN$, $-OG^3$, $-C(O)G^4$, $C(O)NG^5G^6$, $-COOG^7$ and $-SO_3G^8$, wherein $G^1$ to $G^8$ are independently from each other selected from the group consisting of hydrogen, an alkyl group, a cycloalkyl group, an aryl group, and a heteroaryl group; and o is an integer from 1 to 6.

2. The patterned substrate according to claim 1, wherein the dendrimer structures have at least two successive repeating units and the repeating units each have at least two branching points independently from each other.

3. The patterned substrate according to claim 1, wherein the dendrimer structures each have an alkylene silyl group, and the dendrimer structures are connected with the substrate surface via the respective alkylene silyl group.

4. The patterned substrate according to claim 3, wherein the alkylene silyl group has a structure having the following general formula (1)

Formula (1)

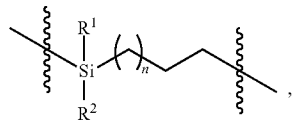

wherein $R^1$ and $R^2$ are independently from each other selected from the group consisting of an alkyl group, a cycloalkyl group, an aryl group, a heteroaryl group, -OA, wherein A is independently from each other selected from the group consisting of an alkyl group, a cycloalkyl group, an aryl group, and a heteroaryl group; and n is an integer from 0 to 6.

5. The patterned substrate according to claim 2, wherein the first dendrimer structures and the second dendrimer structures each have repeating units having the following general formula (2) or (3)

Formula (2)

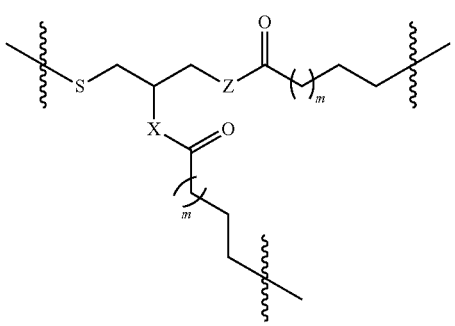

Formula (3)

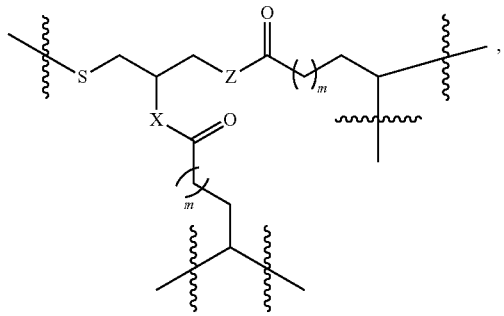

wherein X and Z are independently from each other $NR^3$ or O, wherein each $R^3$ is independently from each other selected from the group consisting of hydrogen, an alkyl group, a cycloalkyl group, an aryl group, and a heteroaryl group; and m is an integer of at least 1.

6. The patterned substrate according to claim 1, wherein the second dendrimer structures have terminal groups having the following general formula (6)

Formula (6)

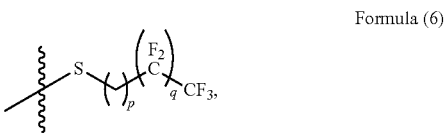

wherein p is an integer from 0 to 10 and q is an integer from 3 to 15.

7. The patterned substrate according to claim 1, wherein the surface of the substrate having the first and second regions has an electrically conductive material.

8. A method for manufacturing a patterned substrate according to claim 1, comprising applying second dendrimer structures in second regions and first dendrimer structures in first regions on a surface of the substrate, wherein the dendrimer structures are each covalently connected with the substrate surface;

the second regions enclose the first regions; and the second dendrimer structures have at least one structural element different from the structural elements of the first dendrimer structures.

9. The method according to claim 8, comprising the steps of (a) providing a substrate, which comprises a surface having hydroxyl groups or silanol groups;

(b) reacting the hydroxyl groups or silanol groups of this surface with an alkenyl silane having the following general formula (12) to form alkenyl silyl groups on the surface Formula (12)

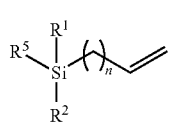

wherein $R^1$ and $R^2$ are independently from each other selected from the group consisting of an alkyl group, a cycloalkyl group, an aryl group, a heteroaryl group, -OA, wherein A is independently from each other selected from the group consisting of an alkyl group, a cycloalkyl group, an aryl group, and a heteroaryl group;

$R^5$ is a halogen or -OQ, wherein Q is selected from the group consisting of an alkyl group, a cycloalkyl group, an aryl group, and a heteroaryl group; and n is an integer from 0 to 6;

(c) reacting with a thiol compound having the following general formula (7)

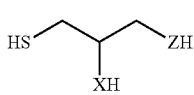

Formula (7)

wherein X and Z are independently from each other $NR^3$ or O, wherein each $R^3$ is independently from each other selected from the group consisting of hydrogen, an alkyl group, a cycloalkyl group, an aryl group, and a heteroaryl group;

(d) reacting with a carboxylic acid having the following general formula (8) or (9)

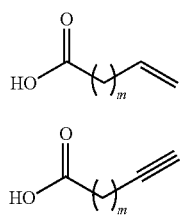

Formula (8)

Formula (9)

wherein m is an integer of at least 1;

(e) at least 1 time repeating the steps (c) and (d) in combination;

(f) selective reacting of a part of the alkenyl or alkynyl groups, which were obtained from the last conducting of step (d), either with (i) a thiol compound having the following general formula (10) to obtain second dendrimer structures

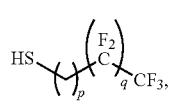

Formula (10)

wherein p is an integer from 0 to 10 and q is an integer from 3 to 15; or with (ii) a thiol compound having the general formula (7) or a thiol compound having the following general formula (11) to obtain first dendrimer structures

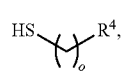

Formula (11)

wherein $R^4$ is selected from the group consisting of -NG$^1$G$^2$, —NO$_2$, —CN, -OG$^3$, —C(O)G$^4$, —C(O)NG$^5$G$^6$, -COOG$^7$ and —SO$_3$G$^8$, wherein G$^1$ to G$^8$ are independently from each other selected from the group consisting of hydrogen, an alkyl group, a cycloalkyl group, an aryl group, and a heteroaryl group; and o is an integer from 1 to 6;

(g) reacting the remaining alkenyl or alkynyl groups either with (i) a thiol compound having the general formula (7) or a thiol compound having the general formula (11) to obtain first dendrimer structures in case second dendrimer structures were formed in step (f); or with (ii) a thiol compound having the general formula (10) to obtain second dendrimer structures in case first dendrimer structures were formed in step (f).

10. The method according to claim 9, wherein step (f) comprises the following steps (f1) to (f4):

(f1) applying the corresponding thiol compound on the surface having alkenyl or alkynyl groups;

(f2) covering the surface having the thiol compound with a photomask;

(f3) irradiating the surface having the thiol compound and the photomask with UV light; and (f4) removing the photomask.

11. The method according to claim 9, wherein step (g) comprises the following steps (g1) and (g2):

(g1) applying the corresponding thiol compound on the surface having the remaining alkenyl or alkynyl groups; and (g2) irradiating the surface having the thiol compound with UV light.

12. A method for the chemical synthesis of a chemical synthesis product, comprising using a patterned substrate according to claim 1 in the method as a characterizing platform and/or as a platform for cell treatment and/or cell cultivation.

13. The method according to claim 12, wherein the patterned substrate is at first used for the chemical synthesis of a chemical synthesis product and then as a characterizing platform for characterizing the chemical synthesis product and/or for treating at least one cell with the chemical synthesis product on the patterned substrate.

14. A patterned substrate comprising first regions and second regions on a surface of the substrate, wherein
the first regions have first dendrimer structures and the second regions have second dendrimer structures;
the dendrimer structures are each covalently connected with the substrate surface;
the second regions enclose the first regions; and
the second dendrimer structures have at least one structural element different from the structural elements of the first dendrimer structures;
wherein the second dendrimer structures have terminal groups having the following general formula (6)

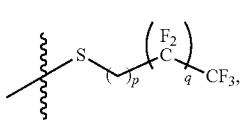

Formula (6)

wherein p is an integer from 0 to 10 and q is an integer from 3 to 15.

15. A method for manufacturing a patterned substrate according to claim 14, comprising applying second dendrimer structures in second regions and first dendrimer structures in first regions on a surface of the substrate,
wherein the dendrimer structures are each covalently connected with the substrate surface;
the second regions enclose the first regions; and
the second dendrimer structures have at least one structural element different from the structural elements of the first dendrimer structures.

16. The method according to claim 15, comprising the steps of
(a) providing a substrate, which comprises a surface having hydroxyl groups or silanol groups;
(b) reacting the hydroxyl groups or silanol groups of this surface with an alkenyl silane having the following general formula (12) to form alkenyl silyl groups on the surface

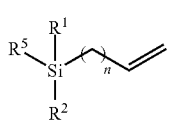

Formula (12)

wherein $R^1$ and $R^2$ are independently from each other selected from the group consisting of an alkyl group, a cycloalkyl group, an aryl group, a heteroaryl group, -OA, wherein A is independently from each other selected from the group consisting of an alkyl group, a cycloalkyl group, an aryl group, and a heteroaryl group;
$R^5$ is a halogen or -OQ, wherein Q is selected from the group consisting of an alkyl group, a cycloalkyl group, an aryl group, and a heteroaryl group; and
n is an integer from 0 to 6;
(c) reacting with a thiol compound having the following general formula (7)

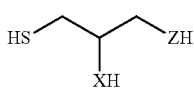

Formula (7)

wherein X and Z are independently from each other $NR^3$ or O, wherein each $R^3$ is independently from each other selected from the group consisting of hydrogen, an alkyl group, a cycloalkyl group, an aryl group, and a heteroaryl group;
(d) reacting with a carboxylic acid having the following general formula (8) or (9)

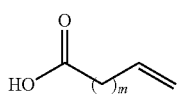

Formula (8)

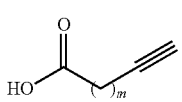

Formula (9)

wherein m is an integer of at least 1;
(e) at least 1 time repeating the steps (c) and (d) in combination;

(f) selective reacting of a part of the alkenyl or alkynyl groups, which were obtained from the last conducting of step (d), either with
(i) a thiol compound having the following general formula (10) to obtain second dendrimer structures

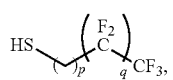

Formula (10)

wherein p is an integer from 0 to 10 and
q is an integer from 3 to 15; or with
(ii) a thiol compound having the general formula (7) or a thiol compound having the following general formula (11) to obtain first dendrimer structures

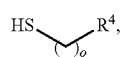

Formula (11)

wherein $R^4$ is selected from the group consisting of $-NG^1G^2$, $-NO_2$, $-CN$, $-OG^3$, $-C(O)G^4$, $-C(O)NG^5G^6$, $-COOG^7$ and $-SO_3G^8$, wherein $G^1$ to $G^8$ are independently from each other selected from the group consisting of hydrogen, an alkyl group, a cycloalkyl group, an aryl group, and a heteroaryl group; and
o is an integer from 1 to 6;
(g) reacting the remaining alkenyl or alkynyl groups either with
(i) a thiol compound having the general formula (7) or a thiol compound having the general formula (11) to obtain first dendrimer structures in case second dendrimer structures were formed in step (f); or with
(ii) a thiol compound having the general formula (10) to obtain second dendrimer structures in case first dendrimer structures were formed in step (f).

17. The method according to claim 16, wherein step (f) comprises the following steps (f1) to (f4):
(f1) applying the corresponding thiol compound on the surface having alkenyl or alkynyl groups;
(f2) covering the surface having the thiol compound with a photomask;
(f3) irradiating the surface having the thiol compound and the photomask with UV light; and
(f4) removing the photomask.

18. The method according to claim 16, wherein step (g) comprises the following steps (g1) and (g2):
(g1) applying the corresponding thiol compound on the surface having the remaining alkenyl or alkynyl groups; and
(g2) irradiating the surface having the thiol compound with UV light.

19. A method for the chemical synthesis of a chemical synthesis product, comprising using a patterned substrate according to claim 14 in the method as a characterizing platform and/or as a platform for cell treatment and/or cell cultivation.

20. The method according to claim 19, wherein the patterned substrate is at first used for the chemical synthesis of a chemical synthesis product and then as a characterizing platform for characterizing the chemical synthesis product and/or for treating at least one cell with the chemical synthesis product on the patterned substrate.

* * * * *